United States Patent [19]

Nagao et al.

[11] Patent Number: 5,723,493

[45] Date of Patent: Mar. 3, 1998

[54] NAPHTHYLOXYACETIC ACID

[75] Inventors: Yuuki Nagao; Takayuki Maruyama; Nobuyuki Hamanaka, all of Mishima-gun, Japan

[73] Assignee: Ono Pharmaceutical Co., Ltd., Osaka, Japan

[21] Appl. No.: 768,291

[22] Filed: Dec. 17, 1996

Related U.S. Application Data

[62] Division of Ser. No. 355,187, Dec. 8, 1994, Pat. No. 5,624,959.

[30] Foreign Application Priority Data

Dec. 9, 1993 [JP] Japan ................................. 5-340854

[51] Int. Cl.$^6$ ................................................ A61K 31/195
[52] U.S. Cl. .................. 514/562; 514/510; 514/604; 560/10; 504/88; 504/89; 504/91; 504/92; 562/427
[58] Field of Search ............................. 560/10; 564/88, 564/89, 91, 92; 562/427; 514/510, 562, 604

Primary Examiner—Samuel Barts
Attorney, Agent, or Firm—Watson Cole Stevens Davis, P.L.L.C.

[57] ABSTRACT

(1) Naphthyloxyaetic acid represented by the compound of the formula (I):

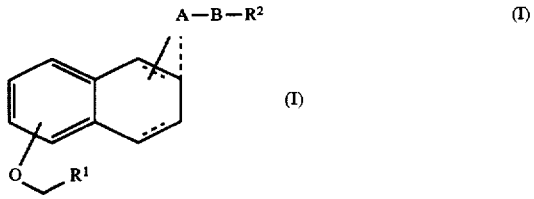

and non-toxic salts thereof.

(2) process for the preparation of the compounds represented by the compound of the formula (I) described hereinbefore.

(3) $PGE_2$ antagonist or agonist containing the compound represented by the compound of the formula (I) as the active ingredient.

The compounds represented by the compounds of the formula (I) can be adapted to medicines which possess an inhibitory effect of uterine contraction, an analgesic action, an inhibitory effect of digestive peristalsis, a sleep-inducing effect as $PGE_2$ antagonists, and an uterine contractile activity, a promoting effect of digestive peristalsis, a suppressive effect of gastric acid secretion, hypotensive activity as $PGE_2$ agonists. The compounds bind to $PGE_2$ receptor and have an activity of antagonist or agonist against the action thereof.

6 Claims, No Drawings

NAPHTHYLOXYACETIC ACID

This application is a division of application Ser. No. 08/355,187 filed Dec. 8, 1994 which application is now U.S. Pat. No. 5,624,959.

SUMMARY

This invention is related to naphthyloxyacetic acid. More particularly, this invention is related to:

(1) a compound of the formula (I):

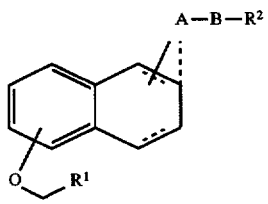

wherein all the symbols are the same meaning as hereafter defined, (2) process for the preparation thereof and (3) prostaglandin $E_2$ (PGE$_2$) antagonists or agonists which comprises naphthyloxyacetic acid or its derivatives as the active ingredient.

BACKGROUND

As prostaglandin (PG)$E_2$ agonists, many compounds are known including PGE$_2$ per se or its derivatives. However, no compounds which antagonize for PGE$_2$ or inhibit PGE$_2$ activity were known until now.

PGE$_2$ is known as a metabolite in the arachidonate cascade. It is known that PGE$_2$ has an uterine contractile activity, a pain-inducing effect, a promoting effect of digestive peristalsis, an awaking effect, a suppressive effect of gastric acid secretion, a hypotensive activity etc. PGE$_2$ exhibits the following expected effects:

To antagonize PGE$_2$ means to suppress the effects above mentioned. Therefore PGE$_2$ antagonists are considered to inhibit uterine contraction, to have an analgesic action, to inhibit digestive peristalsis, to induce sleep, etc. Therefore, PGE$_2$ antagonists are considered to be useful as analgesics, antidiarrheals, sleep inducers or for the preventive of abortion.

To agonize for PGE$_2$ means to promote the effects above mentioned, so PGE$_2$ agonists are considered to promote uterine contraction, to promote digestive peristalsis, to suppress a gastric acid secretion, to lower blood pressure. Therefore, PGE$_2$ agonists are considered to be useful for abortion, cathartics, antiulcer, anti-gastritis, antihypertensivity.

DISCLOSURE OF THE INVENTION

The present invention is related to novel compounds, use of the novel compounds and process for the preparation of the novel compounds.

Accordingly, the present invention is related to (1) naphthyloxyacetic acid derivatives of the formula (I):

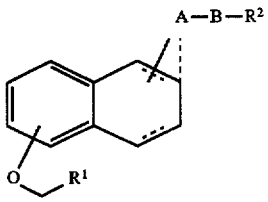

wherein

R$^1$ is (i) —COOR$^4$ in which R$^4$ is hydrogen or C1–4 alkyl, (ii) —CONR$^5$R$^6$ in which R$^5$ and R$^6$ each, independently, is hydrogen, C1–4 alkyl or C1–4 alkyl substituted by 1 of hydroxy, (iii) —CH$_2$OH,

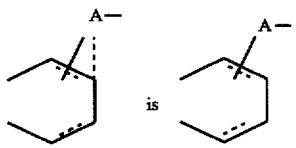

in which A is a bond or a C1–4 alkylene, or

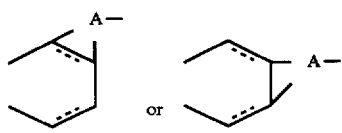

in which A is

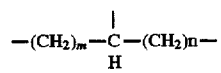

in which m is 0, 1, 2, 3, 4, n is 0, 1, 2, 3, 4, and m+n is 2, 3, 4;

B is —NR$^3$SO$_2$— or —SO$_2$NR$^3$— in which R$^3$ is hydrogen, C1–4 alkyl or —CH$_2$COOR$^7$ in which R$^7$ is hydrogen or R$^{4a}$, in which R$^{4a}$ is C1–4 alkyl;

R$^2$ is (i) C1–6 alkyl, C2–6 alkenyl or C2–6 alkynyl, or (ii) C1–6 alkyl, C2–6 alkenyl or C2–6 alkynyl substituted by 1, 2, 3 of the following substituents: phenyl, C4–7 cycloalkyl or phenyl substituted by 1, 2, 3 of the following: C1–4 alkyl, C1–4 alkoxy or halogen or (iii) naphthyl;

in the formula

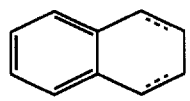

- - - - is a bond or a double bond;

or non-toxic acid thereof, (2) process for the preparation thereof and (3) prostaglandin $E_2$ (PGE$_2$) antagonists or agonists which comprises naphthyloxyacetic acid or its derivatives as active ingredient.

In the formula (I), C1–4 alkyl represented by R$^3$, R$^4$, R$^5$, R$^6$, R$^7$ means methyl, ethyl, propyl, butyl and isomeric groups thereof.

In the formula (I), C1–6 alkyl represented by R$^2$ means methyl, ethyl, propyl, butyl, pentyl, hexyl and isomeric groups thereof.

In the formula (I), C2–6 alkenyl represented by R² means vinyl, propenyl, butenyl, pentenyl, hexenyl and isomeric groups thereof.

In the formula (I), C2–6 alkynyl represented by R² means ethynyl, propynyl, butynyl, pentynyl, hexynyl and isomeric groups thereof.

In the formula (I), C4–7 cycloalkyl represented by R² means cyclobutyl, cyclopentyl, cyclohexyl, cycloheptyl.

In the formula (I), the C1–4 alkyl substituents of phenyl in R² means methyl, ethyl, propyl, butyl and isomeric groups thereof.

In the formula (I), the C1–4 alkoxy substituents of phenyl in R² means methoxy, ethoxy, propoxy, butoxy and isomeric groups thereof.

In the formula (I), the halogen substitutents of phenyl in R² means fluorine, chlorine, bromine and iodine.

In the formula (I), C1–4 alkylene represented by A means methylene, ethylene, trimethylene, tetramethylene and isomeric groups thereof.

In the formula (I), the ring represented by

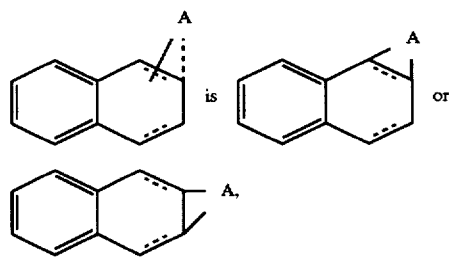

for example,

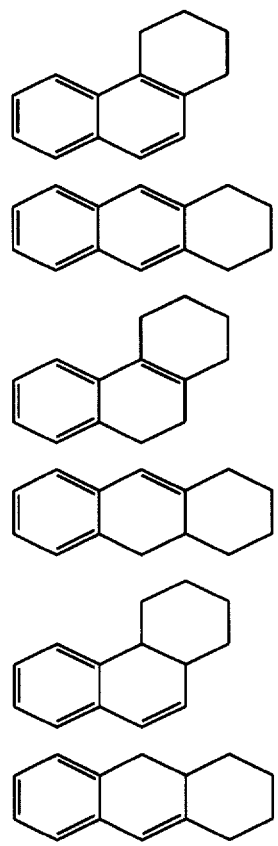

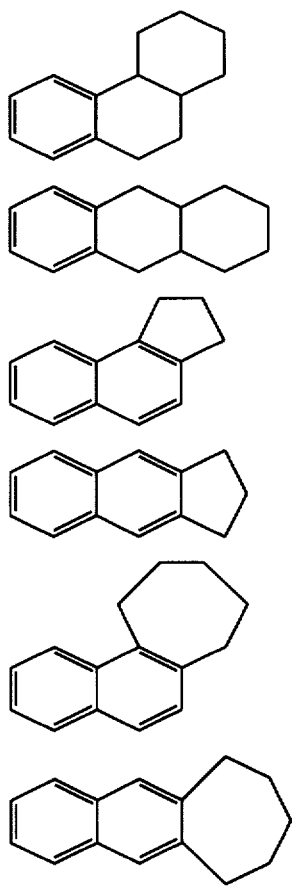

Unless otherwise, specified all isomers are included in the invention. For example, alkyl, alkylene and alkenylene includes straight-chain or branched-chain isomers. Double bonds in alkenylene include structure of configurations E, Z and E, Z mixtures. Isomers generated by asymmetric carbon (s) e.g. branched alkyl are also included within the present invention.

PREFERABLE COMPOUNDS

In the structure of formula (I) of the present invention, the compounds described in Example and the following compounds are preferable.

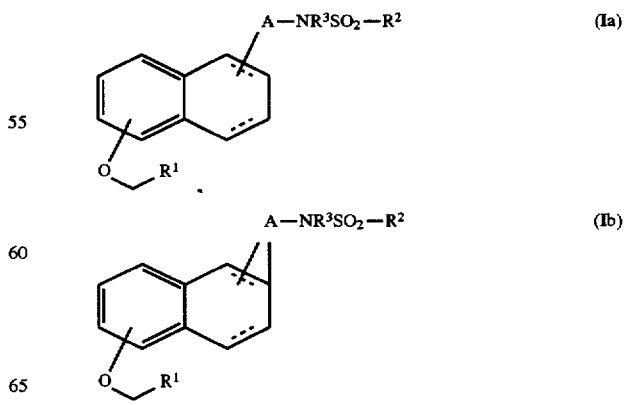

-continued

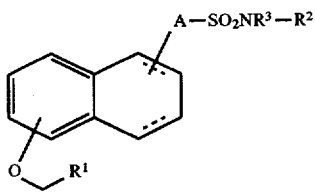

(Id)

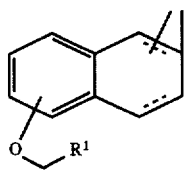

(Ie)

wherein all the symbols are the same meaning as hereinbefore defined.

Especially preferable compounds are the compounds described in Example and the following compounds.

| $R^1$ | A | $R^3$ | $R^2$ |
|---|---|---|---|

(Ia-1)

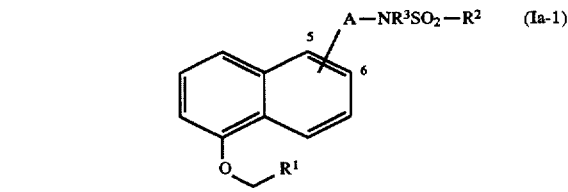

| $R^1$ | A | $R^3$ | $R^2$ |
|---|---|---|---|
| —COOH | 5-bond | hydrogen | 2,2-diphenylethyl |
| —COOH | 5-bond | hydrogen | 2-naphthyl |
| —COOH | 5-bond | hydrogen | 2-(4-methoxyphenyl)vinyl |
| —COOH | 5-bond | hydrogen | 2-(4-chlorophenyl)vinyl |
| —COOH | 5-bond | hydrogen | 2-phenyl-2-(4-methoxyphenyl)vinyl |
| —COOH | 5-bond | hydrogen | 2-phenyl-2-(4-chlorophenyl)vinyl |
| —COOH | 5-bond | hydrogen | 2-(4-methoxyphenyl)ethyl |
| —COOH | 5-bond | hydrogen | 2-(4-chlorophenyl)ethyl |
| —COOH | 5-bond | hydrogen | 2-phenyl-2-(4-methoxyphenyl)ethyl |
| —COOH | 5-bond | hydrogen | 2-phenyl-2-(4-chlorophenyl)ethyl |
| —COOH | 5-bond | methyl | 2-phenylvinyl |
| —COOH | 5-bond | methyl | 2,2-diphenylvinyl |
| —COOH | 5-bond | methyl | 2-phenylethyl |
| —COOH | 5-bond | methyl | 2,2-diphenylethyl |
| —COOH | 5-bond | methyl | pentyl |
| —COOH | 5-bond | methyl | 2-naphthyl |
| —COOH | 5-bond | methyl | 2-(4-methoxyphenyl)vinyl |
| —COOH | 5-bond | methyl | 2-(4-chlorophenyl)vinyl |
| —COOH | 5-bond | methyl | 2-phenyl-2-(4-methoxyphenyl)vinyl |
| —COOH | 5-bond | methyl | 2-phenyl-2-(4-chlorophenyl)vinyl |
| —COOH | 5-bond | methyl | 2-(4-methoxyphenyl)ethyl |
| —COOH | 5-bond | methyl | 2-(4-chlorophenyl)ethyl |
| —COOH | 5-bond | methyl | 2-phenyl-2-(4-methoxyphenyl)ethyl |
| —COOH | 5-bond | methyl | 2-phenyl-2-(4-chlorophenyl)ethyl |
| —COOH | 5-bond | —CH$_2$COOH | 2-phenylvinyl |
| —COOH | 5-bond | —CH$_2$COOH | 2,2-diphenylvinyl |
| —COOH | 5-bond | —CH$_2$COOH | 2-phenylethyl |
| —COOH | 5-bond | —CH$_2$COOH | 2,2-diphenylethyl |
| —COOH | 5-bond | —CH$_2$COOH | pentyl |
| —COOH | 5-bond | —CH$_2$COOH | 2-naphthyl |
| —COOH | 5-bond | —CH$_2$COOH | 2-(4-methoxyphenyl)vinyl |
| —COOH | 5-bond | —CH$_2$COOH | 2-(4-chlorophenyl)vinyl |
| —COOH | 5-bond | —CH$_2$COOH | 2-phenyl-2-(4-methoxyphenyl)vinyl |
| —COOH | 5-bond | —CH$_2$COOH | 2-phenyl-2-(4-chlorophenyl)vinyl |
| —COOH | 5-bond | —CH$_2$COOH | 2-(4-methoxyphenyl)ethyl |
| —COOH | 5-bond | —CH$_2$COOH | 2-(4-chlorophenyl)ethyl |
| —COOH | 5-bond | —CH$_2$COOH | 2-phenyl-2-(4-methoxyphenyl)ethyl |
| —COOH | 5-bond | —CH$_2$COOH | 2-phenyl-2-(4-chlorophenyl)ethyl |
| —COOH | 5-CH$_2$CH$_2$ | hydrogen | pentyl |
| —COOH | 5-CH$_2$CH$_2$ | hydrogen | 2-naphthyl |
| —COOH | 5-CH$_2$CH$_2$ | hydrogen | 2-(4-methoxyphenyl)vinyl |
| —COOH | 5-CH$_2$CH$_2$ | hydrogen | 2-(4-chlorophenyl)vinyl |

-continued

| R¹ | A | R³ | R² |
|---|---|---|---|
| —COOH | 5-CH₂CH₂ | hydrogen | 2-phenyl-2-(4-methoxyphenyl)vinyl |
| —COOH | 5-CH₂CH₂ | hydrogen | 2-phenyl-2-(4-chlorophenyl)vinyl |
| —COOH | 5-CH₂CH₂ | hydrogen | 2-(4-methoxyphenyl)ethyl |
| —COOH | 5-CH₂CH₂ | hydrogen | 2-(4-chlorophenyl)ethyl |
| —COOH | 5-CH₂CH₂ | hydrogen | 2-phenyl-2-(4-methoxyphenyl)ethyl |
| —COOH | 5-CH₂CH₂ | hydrogen | 2-phenyl-2-(4-chlorophenyl)ethyl |
| —COOH | 5-CH₂CH₂ | methyl | 2,2-diphenylvinyl |
| —COOH | 5-CH₂CH₂ | methyl | 2-phenylethyl |
| —COOH | 5-CH₂CH₂ | methyl | 2,2-diphenylethyl |
| —COOH | 5-CH₂CH₂ | methyl | pentyl |
| —COOH | 5-CH₂CH₂ | methyl | 2-naphthyl |
| —COOH | 5-CH₂CH₂ | methyl | 2-(4-methoxyphenyl)vinyl |
| —COOH | 5-CH₂CH₂ | methyl | 2-(4-chlorophenyl)vinyl |
| —COOH | 5-CH₂CH₂ | methyl | 2-phenyl-2-(4-methoxyphenyl)vinyl |
| —COOH | 5-CH₂CH₂ | methyl | 2-phenyl-2-(4-chlorophenyl)vinyl |
| —COOH | 5-CH₂CH₂ | methyl | 2-(4-methoxyphenyl)ethyl |
| —COOH | 5-CH₂CH₂ | methyl | 2-(4-chlorophenyl)ethyl |
| —COOH | 5-CH₂CH₂ | methyl | 2-phenyl-2-(4-methoxyphenyl)ethyl |
| —COOH | 5-CH₂CH₂ | methyl | 2-phenyl-2-(4-chlorophenyl)ethyl |
| —COOH | 5-CH₂CH₂ | —CH₂COOH | 2,2-diphenylvinyl |
| —COOH | 5-CH₂CH₂ | —CH₂COOH | 2-phenylethyl |
| —COOH | 5-CH₂CH₂ | —CH₂COOH | 2,2-diphenylethyl |
| —COOH | 5-CH₂CH₂ | —CH₂COOH | pentyl |
| —COOH | 5-CH₂CH₂ | —CH₂COOH | 2-naphthyl |
| —COOH | 5-CH₂CH₂ | —CH₂COOH | 2-(4-methoxyphenyl)vinyl |
| —COOH | 5-CH₂CH₂ | —CH₂COOH | 2-(4-chlorophenyl)vinyl |
| —COOH | 5-CH₂CH₂ | —CH₂COOH | 2-phenyl-2-(4-methoxyphenyl)vinyl |
| —COOH | 5-CH₂CH₂ | —CH₂COOH | 2-phenyl-2-(4-chlorophenyl)vinyl |
| —COOH | 5-CH₂CH₂ | —CH₂COOH | 2-(4-methoxyphenyl)ethyl |
| —COOH | 5-CH₂CH₂ | —CH₂COOH | 2-(4-chlorophenyl)ethyl |
| —COOH | 5-CH₂CH₂ | —CH₂COOH | 2-phenyl-2-(4-methoxyphenyl)ethyl |
| —COOH | 5-CH₂CH₂ | —CH₂COOH | 2-phenyl-2-(4-chlorophenyl)ethyl |
| —COOH | 6-bond | hydrogen | 2-phenylethyl |
| —COOH | 6-bond | hydrogen | 2,2-diphenylethyl |
| —COOH | 6-bond | hydrogen | pentyl |
| —COOH | 6-bond | hydrogen | 2-naphthyl |
| —COOH | 6-bond | hydrogen | 2-(4-methoxyphenyl)vinyl |
| —COOH | 6-bond | hydrogen | 2-(4-chlorophenyl)vinyl |
| —COOH | 6-bond | hydrogen | 2-phenyl-2-(4-methoxyphenyl)vinyl |
| —COOH | 6-bond | hydrogen | 2-phenyl-2-(4-chlorophenyl)vinyl |
| —COOH | 6-bond | hydrogen | 2-(4-methoxyphenyl)ethyl |
| —COOH | 6-bond | hydrogen | 2-(4-chlorophenyl)ethyl |
| —COOH | 6-bond | hydrogen | 2-phenyl-2-(4-methoxyphenyl)ethyl |
| —COOH | 6-bond | hydrogen | 2-phenyl-2-(4-chlorophenyl)ethyl |
| —COOH | 6-CH₂CH₂ | hydrogen | 2-phenylethyl |
| —COOH | 6-CH₂CH₂ | hydrogen | 2,2-diphenylethyl |
| —COOH | 6-CH₂CH₂ | hydrogen | pentyl |
| —COOH | 6-CH₂CH₂ | hydrogen | 2-naphthyl |
| —COOH | 6-CH₂CH₂ | hydrogen | 2-(4-methoxyphenyl)vinyl |
| —COOH | 6-CH₂CH₂ | hydrogen | 2-(4-chlorophenyl)vinyl |
| —COOH | 6-CH₂CH₂ | hydrogen | 2-phenyl-2-(4-methoxyphenyl)vinyl |
| —COOH | 6-CH₂CH₂ | hydrogen | 2-phenyl-2-(4-chlorophenyl)vinyl |
| —COOH | 6-CH₂CH₂ | hydrogen | 2-(4-methoxyphenyl)ethyl |
| —COOH | 6-CH₂CH₂ | hydrogen | 2-(4-chlorophenyl)ethyl |
| —COOH | 6-CH₂CH₂ | hydrogen | 2-phenyl-2-(4-methoxyphenyl)ethyl |
| —COOH | 6-CH₂CH₂ | hydrogen | 2-phenyl-2-(4-chlorophenyl)ethyl |
| —CONH₂ | 5-bond | hydrogen | 2-phenylvinyl |
| —CONH₂ | 5-bond | hydrogen | 2,2-diphenylvinyl |
| —CONH₂ | 5-bond | hydrogen | 2-phenylethyl |
| —CONH₂ | 5-bond | hydrogen | 2,2-diphenylethyl |
| —CONH₂ | 5-bond | hydrogen | pentyl |
| —CONH₂ | 5-bond | hydrogen | 2-naphthyl |
| —CONH₂ | 5-bond | hydrogen | 2-(4-methoxyphenyl)vinyl |
| —CONH₂ | 5-bond | hydrogen | 2-(4-chlorophenyl)vinyl |
| —CONH₂ | 5-bond | hydrogen | 2-phenyl-2-(4-methoxyphenyl)vinyl |
| —CONH₂ | 5-bond | hydrogen | 2-phenyl-2-(4-chlorophenyl)vinyl |
| —CONH₂ | 5-bond | hydrogen | 2-(4-methoxyphenyl)ethyl |
| —CONH₂ | 5-bond | hydrogen | 2-(4-chlorophenyl)ethyl |
| —CONH₂ | 5-bond | hydrogen | 2-phenyl-2-(4-methoxyphenyl)ethyl |
| —CONH₂ | 5-bond | hydrogen | 2-phenyl-2-(4-chlorophenyl)ethyl |
| —CONH₂ | 5-CH₂CH₂ | hydrogen | 2,2-diphenylvinyl |
| —CONH₂ | 5-CH₂CH₂ | hydrogen | 2-phenylethyl |
| —CONH₂ | 5-CH₂CH₂ | hydrogen | 2,2-diphenylethyl |
| —CONH₂ | 5-CH₂CH₂ | hydrogen | pentyl |
| —CONH₂ | 5-CH₂CH₂ | hydrogen | 2-naphthyl |
| —CONH₂ | 5-CH₂CH₂ | hydrogen | 2-(4-methoxyphenyl)vinyl |
| —CONH₂ | 5-CH₂CH₂ | hydrogen | 2-(4-chlorophenyl)vinyl |
| —CONH₂ | 5-CH₂CH₂ | hydrogen | 2-phenyl-2-(4-methoxyphenyl)vinyl |

-continued

| R¹ | A | R³ | R² |
|---|---|---|---|
| —CONH₂ | 5-CH₂CH₂ | hydrogen | 2-phenyl-2-(4-chlorophenyl)vinyl |
| —CONH₂ | 5-CH₂CH₂ | hydrogen | 2-(4-methoxyphenyl)ethyl |
| —CONH₂ | 5-CH₂CH₂ | hydrogen | 2-(4-chlorophenyl)ethyl |
| —CONH₂ | 5-CH₂CH₂ | hydrogen | 2-phenyl-2-(4-methoxyphenyl)ethyl |
| —CONH₂ | 5-CH₂CH₂ | hydrogen | 2-phenyl-2-(4-chlorophenyl)ethyl |
| —CH₂OH | 5-bond | hydrogen | 2-phenylvinyl |
| —CH₂OH | 5-bond | hydrogen | 2,2-diphenylvinyl |
| —CH₂OH | 5-bond | hydrogen | 2-phenylethyl |
| —CH₂OH | 5-bond | hydrogen | 2,2-diphenylethyl |
| —CH₂OH | 5-bond | hydrogen | pentyl |
| —CH₂OH | 5-bond | hydrogen | 2-naphthyl |
| —CH₂OH | 5-bond | hydrogen | 2-(4-methoxyphenyl)vinyl |
| —CH₂OH | 5-bond | hydrogen | 2-(4-chlorophenyl)vinyl |
| —CH₂OH | 5-bond | hydrogen | 2-phenyl-2-(4-methoxyphenyl)vinyl |
| —CH₂OH | 5-bond | hydrogen | 2-phenyl-2-(4-chlorophenyl)vinyl |
| —CH₂OH | 5-bond | hydrogen | 2-(4-methoxyphenyl)ethyl |
| —CH₂OH | 5-bond | hydrogen | 2-(4-chlorophenyl)ethyl |
| —CH₂OH | 5-bond | hydrogen | 2-phenyl-2-(4-methoxyphenyl)ethyl |
| —CH₂OH | 5-bond | hydrogen | 2-phenyl-2-(4-chlorophenyl)ethyl |
| —CH₂OH | 5-CH₂CH₂ | hydrogen | 2,2-diphenylvinyl |
| —CH₂OH | 5-CH₂CH₂ | hydrogen | 2-phenylethyl |
| —CH₂OH | 5-CH₂CH₂ | hydrogen | 2,2-diphenylethyl |
| —CH₂OH | 5-CH₂CH₂ | hydrogen | pentyl |
| —CH₂OH | 5-CH₂CH₂ | hydrogen | 2-naphthyl |
| —CH₂OH | 5-CH₂CH₂ | hydrogen | 2-(4-methoxyphenyl)vinyl |
| —CH₂OH | 5-CH₂CH₂ | hydrogen | 2-(4-chlorophenyl)vinyl |
| —CH₂OH | 5-CH₂CH₂ | hydrogen | 2-phenyl-2-(4-methoxyphenyl)vinyl |
| —CH₂OH | 5-CH₂CH₂ | hydrogen | 2-phenyl-2-(4-chlorophenyl)vinyl |
| —CH₂OH | 5-CH₂CH₂ | hydrogen | 2-(4-methoxyphenyl)ethyl |
| —CH₂OH | 5-CH₂CH₂ | hydrogen | 2-(4-chlorophenyl)ethyl |
| —CH₂OH | 5-CH₂CH₂ | hydrogen | 2-phenyl-2-(4-methoxyphenyl)ethyl |
| —CH₂OH | 5-CH₂CH₂ | hydrogen | 2-phenyl-2-(4-chlorophenyl)ethyl |

(Id-1)

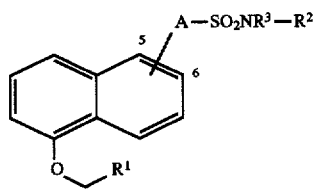

| R¹ | A | R³ | R² |
|---|---|---|---|
| —COOH | 5-bond | hydrogen | pentyl |
| —COOH | 5-bond | hydrogen | 2-naphthyl |
| —COOH | 5-bond | hydrogen | 2-(4-methoxyphenyl)ethyl |
| —COOH | 5-bond | hydrogen | 2-(4-chlorophenyl)ethyl |
| —COOH | 5-bond | hydrogen | 2-phenyl-2-(4-methoxyphenyl)ethyl |
| —COOH | 5-bond | hydrogen | 2-phenyl-2-(4-chlorophenyl)ethyl |
| —COOH | 5-bond | methyl | 2-phenylethyl |
| —COOH | 5-bond | methyl | 2,2-diphenylethyl |
| —COOH | 5-bond | methyl | pentyl |
| —COOH | 5-bond | methyl | 2-naphthyl |
| —COOH | 5-bond | methyl | 2-(4-methoxyphenyl)ethyl |
| —COOH | 5-bond | methyl | 2-(4-chlorophenyl)ethyl |
| —COOH | 5-bond | methyl | 2-phenyl-2-(4-methoxyphenyl)ethyl |
| —COOH | 5-bond | methyl | 2-phenyl-2-(4-chlorophenyl)ethyl |
| —COOH | 5-bond | —CH₂COOH | 2-phenylethyl |
| —COOH | 5-bond | —CH₂COOH | 2,2-diphenylethyl |
| —COOH | 5-bond | —CH₂COOH | pentyl |
| —COOH | 5-bond | —CH₂COOH | 2-naphthyl |
| —COOH | 5-bond | —CH₂COOH | 2-(4-methoxyphenyl)ethyl |
| —COOH | 5-bond | —CH₂COOH | 2-(4-chlorophenyl)ethyl |
| —COOH | 5-bond | —CH₂COOH | 2-phenyl-2-(4-methoxyphenyl)ethyl |
| —COOH | 5-bond | —CH₂COOH | 2-phenyl-2-(4-chlorophenyl)ethyl |
| —COOH | 5-CH₂CH₂ | hydrogen | pentyl |
| —COOH | 5-CH₂CH₂ | hydrogen | 2-naphthyl |
| —COOH | 5-CH₂CH₂ | hydrogen | 2-(4-methoxyphenyl)ethyl |
| —COOH | 5-CH₂CH₂ | hydrogen | 2-(4-chlorophenyl)ethyl |
| —COOH | 5-CH₂CH₂ | hydrogen | 2-phenyl-2-(4-methoxyphenyl)ethyl |
| —COOH | 5-CH₂CH₂ | hydrogen | 2-phenyl-2-(4-chlorophenyl)ethyl |
| —COOH | 5-CH₂CH₂ | methyl | 2-phenylethyl |
| —COOH | 5-CH₂CH₂ | methyl | 2,2-diphenylethyl |
| —COOH | 5-CH₂CH₂ | methyl | pentyl |
| —COOH | 5-CH₂CH₂ | methyl | 2-naphthyl |
| —COOH | 5-CH₂CH₂ | methyl | 2-(4-methoxyphenyl)ethyl |

-continued

| $R^1$ | A | $R^3$ | $R^2$ |
|---|---|---|---|
| —COOH | 5-$CH_2CH_2$ | methyl | 2-(4-chlorophenyl)ethyl |
| —COOH | 5-$CH_2CH_2$ | methyl | 2-phenyl-2-(4-methoxyphenyl)ethyl |
| —COOH | 5-$CH_2CH_2$ | methyl | 2-phenyl-2-(4-chlorophenyl)ethyl |
| —COOH | 5-$CH_2CH_2$ | —$CH_2COOH$ | 2-phenylethyl |
| —COOH | 5-$CH_2CH_2$ | —$CH_2COOH$ | 2,2-diphenylethyl |
| —COOH | 5-$CH_2CH_2$ | —$CH_2COOH$ | pentyl |
| —COOH | 5-$CH_2CH_2$ | —$CH_2COOH$ | 2-naphthyl |
| —COOH | 5-$CH_2CH_2$ | —$CH_2COOH$ | 2-(4-methoxyphenyl)ethyl |
| —COOH | 5-$CH_2CH_2$ | —$CH_2COOH$ | 2-(4-chlorophenyl)ethyl |
| —COOH | 5-$CH_2CH_2$ | —$CH_2COOH$ | 2-phenyl-2-(4-methoxyphenyl)ethyl |
| —COOH | 5-$CH_2CH_2$ | —$CH_2COOH$ | 2-phenyl-2-(4-chlorophenyl)ethyl |
| —COOH | 6-bond | hydrogen | 2-phenylethyl |
| —COOH | 6-bond | hydrogen | 2,2-diphenylethyl |
| —COOH | 6-bond | hydrogen | pentyl |
| —COOH | 6-bond | hydrogen | 2-naphthyl |
| —COOH | 6-bond | hydrogen | 2-(4-methoxyphenyl)ethyl |
| —COOH | 6-bond | hydrogen | 2-(4-chlorophenyl)ethyl |
| —COOH | 6-bond | hydrogen | 2-phenyl-2-(4-methoxyphenyl)ethyl |
| —COOH | 6-bond | hydrogen | 2-phenyl-2-(4-chlorophenyl)ethyl |
| —COOH | 6-$CH_2CH_2$ | hydrogen | 2-phenylethyl |
| —COOH | 6-$CH_2CH_2$ | hydrogen | 2,2-diphenylethyl |
| —COOH | 6-$CH_2CH_2$ | hydrogen | pentyl |
| —COOH | 6-$CH_2CH_2$ | hydrogen | 2-naphthyl |
| —COOH | 6-$CH_2CH_2$ | hydrogen | 2-(4-methoxyphenyl)ethyl |
| —COOH | 6-$CH_2CH_2$ | hydrogen | 2-(4-chlorophenyl)ethyl |
| —COOH | 6-$CH_2CH_2$ | hydrogen | 2-phenyl-2-(4-methoxyphenyl)ethyl |
| —COOH | 6-$CH_2CH_2$ | hydrogen | 2-phenyl-2-(4-chlorophenyl)ethyl |
| —$CONH_2$ | 5-bond | hydrogen | 2-phenylethyl |
| —$CONH_2$ | 5-bond | hydrogen | 2,2-diphenylethyl |
| —$CONH_2$ | 5-bond | hydrogen | pentyl |
| —$CONH_2$ | 5-bond | hydrogen | 2-naphthyl |
| —$CONH_2$ | 5-bond | hydrogen | 2-(4-methoxyphenyl)ethyl |
| —$CONH_2$ | 5-bond | hydrogen | 2-(4-chlorophenyl)ethyl |
| —$CONH_2$ | 5-bond | hydrogen | 2-phenyl-2-(4-methoxyphenyl)ethyl |
| —$CONH_2$ | 5-bond | hydrogen | 2-phenyl-2-(4-chlorophenyl)ethyl |
| —$CONH_2$ | 5-$CH_2CH_2$ | hydrogen | 2-phenylethyl |
| —$CONH_2$ | 5-$CH_2CH_2$ | hydrogen | 2,2-diphenylethyl |
| —$CONH_2$ | 5-$CH_2CH_2$ | hydrogen | pentyl |
| —$CONH_2$ | 5-$CH_2CH_2$ | hydrogen | 2-naphthyl |
| —$CONH_2$ | 5-$CH_2CH_2$ | hydrogen | 2-(4-methoxyphenyl)ethyl |
| —$CONH_2$ | 5-$CH_2CH_2$ | hydrogen | 2-(4-chlorophenyl)ethyl |
| —$CONH_2$ | 5-$CH_2CH_2$ | hydrogen | 2-phenyl-2-(4-methoxyphenyl)ethyl |
| —$CONH_2$ | 5-$CH_2CH_2$ | hydrogen | 2-phenyl-2-(4-chlorophenyl)ethyl |
| —$CH_2OH$ | 5-bond | hydrogen | 2-phenylethyl |
| —$CH_2OH$ | 5-bond | hydrogen | 2,2-diphenylethyl |
| —$CH_2OH$ | 5-bond | hydrogen | pentyl |
| —$CH_2OH$ | 5-bond | hydrogen | 2-naphthyl |
| —$CH_2OH$ | 5-bond | hydrogen | 2-(4-methoxyphenyl)ethyl |
| —$CH_2OH$ | 5-bond | hydrogen | 2-(4-chlorophenyl)ethyl |
| —$CH_2OH$ | 5-bond | hydrogen | 2-phenyl-2-(4-methoxyphenyl)ethyl |
| —$CH_2OH$ | 5-bond | hydrogen | 2-phenyl-2-(4-chlorophenyl)ethyl |
| —$CH_2OH$ | 5-$CH_2CH_2$ | hydrogen | 2-phenylethyl |
| —$CH_2OH$ | 5-$CH_2CH_2$ | hydrogen | 2,2-diphenylethyl |
| —$CH_2OH$ | 5-$CH_2CH_2$ | hydrogen | pentyl |
| —$CH_2OH$ | 5-$CH_2CH_2$ | hydrogen | 2-naphthyl |
| —$CH_2OH$ | 5-$CH_2CH_2$ | hydrogen | 2-(4-methoxyphenyl)ethyl |
| —$CH_2OH$ | 5-$CH_2CH_2$ | hydrogen | 2-(4-chlorophenyl)ethyl |
| —$CH_2OH$ | 5-$CH_2CH_2$ | hydrogen | 2-phenyl-2-(4-methoxyphenyl)ethyl |
| —$CH_2OH$ | 5-$CH_2CH_2$ | hydrogen | 2-phenyl-2-(4-chlorophenyl)ethyl |

(Ia-2)

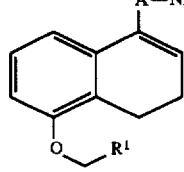

| | | |
|---|---|---|
| —COOH | bond | 2,2-diphenylvinyl |
| —COOH | bond | 2,2-diphenylethyl |
| —COOH | —$CH_2CH_2$— | 2-phenylvinyl |
| —COOH | —$CH_2CH_2$— | 2,2-diphenylvinyl |
| —COOH | —$CH_2CH_2$— | 2-phenylethyl |
| —COOH | —$CH_2CH_2$— | 2,2-diphenylethyl |

-continued

| R¹ | A | R³ | R² |
|---|---|---|---|
| —CONH₂ | bond | | 2-phenylvinyl |
| —CONH₂ | bond | | 2,2-diphenylvinyl |
| —CONH₂ | bond | | 2-phenylethyl |
| —CONH₂ | bond | | 2,2-diphenylethyl |
| —CONH₂ | —CH₂CH₂— | | 2-phenylvinyl |
| —CONH₂ | —CH₂CH₂— | | 2,2-diphenylvinyl |
| —CONH₂ | —CH₂CH₂— | | 2-phenylethyl |
| —CONH₂ | —CH₂CH₂— | | 2,2-diphenylethyl |

(Id-2)

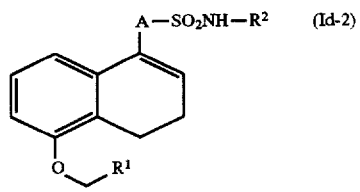

| R¹ | A | R³ | R² |
|---|---|---|---|
| —COOH | bond | | 2-phenylvinyl |
| —COOH | bond | | 2,2-diphenylvinyl |
| —COOH | bond | | 2-phenylethyl |
| —COOH | bond | | 2,2-diphenylethyl |
| —COOH | —CH₂CH₂— | | 2-phenylvinyl |
| —COOH | —CH₂CH₂— | | 2,2-diphenylvinyl |
| —COOH | —CH₂CH₂— | | 2-phenylethyl |
| —COOH | —CH₂CH₂— | | 2,2-diphenylethyl |
| —CONH₂ | bond | | 2-phenylvinyl |
| —CONH₂ | bond | | 2,2-diphenylvinyl |
| —CONH₂ | bond | | 2-phenylethyl |
| —CONH₂ | bond | | 2,2-diphenylethyl |
| —CONH₂ | —CH₂CH₂— | | 2-phenylvinyl |
| —CONH₂ | —CH₂CH₂— | | 2,2-diphenylvinyl |
| —CONH₂ | —CH₂CH₂— | | 2-phenylethyl |
| —CONH₂ | —CH₂CH₂— | | 2,2-diphenylethyl |

(Ia-3)

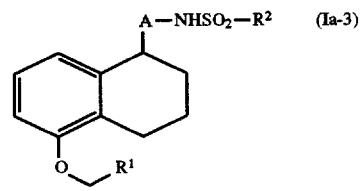

| R¹ | A | R³ | R² |
|---|---|---|---|
| —COOH | bond | | 2-phenylethyl |
| —COOH | bond | | 2,2-diphenylethyl |
| —COOH | —CH₂CH₂— | | 2,2-diphenylvinyl |
| —COOH | —CH₂CH₂— | | 2-phenylethyl |
| —COOH | —CH₂CH₂— | | 2,2-diphenylethyl |
| —CONH₂ | bond | | 2-phenylvinyl |
| —CONH₂ | bond | | 2,2-diphenylvinyl |
| —CONH₂ | bond | | 2-phenylethyl |
| —CONH₂ | bond | | 2,2-diphenylethyl |
| —CONH₂ | —CH₂CH₂— | | 2-phenylvinyl |
| —CONH₂ | —CH₂CH₂— | | 2,2-diphenylvinyl |
| —CONH₂ | —CH₂CH₂— | | 2-phenylethyl |
| —CONH₂ | —CH₂CH₂— | | 2,2-diphenylethyl |

(Id-3)

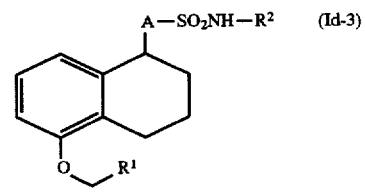

| R¹ | A | R³ | R² |
|---|---|---|---|
| —COOH | bond | | 2-phenylvinyl |
| —COOH | bond | | 2,2-diphenylvinyl |
| —COOH | bond | | 2-phenylethyl |

-continued

| R¹ | A | R³ | R² |
|---|---|---|---|
| —COOH | bond | | 2,2-diphenylethyl |
| —COOH | —CH₂CH₂— | | 2-phenylvinyl |
| —COOH | —CH₂CH₂— | | 2,2-diphenylvinyl |
| —COOH | —CH₂CH₂— | | 2-phenylethyl |
| —COOH | —CH₂CH₂— | | 2,2-diphenylethyl |
| —CONH₂ | bond | | 2-phenylvinyl |
| —CONH₂ | bond | | 2,2-diphenylvinyl |
| —CONH₂ | bond | | 2-phenylethyl |
| —CONH₂ | bond | | 2,2-diphenylethyl |
| —CONH₂ | —CH₂CH₂— | | 2-phenylvinyl |
| —CONH₂ | —CH₂CH₂— | | 2,2-diphenylvinyl |
| —CONH₂ | —CH₂CH₂— | | 2-phenylethyl |
| —CONH₂ | —CH₂CH₂— | | 2,2-diphenylethyl |

(Ib-1)

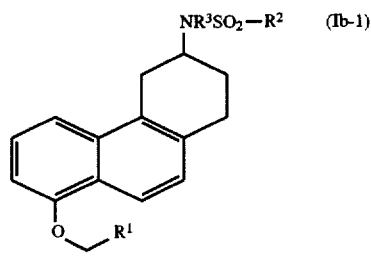

| R¹ | R³ | R² |
|---|---|---|
| —COOH | hydrogen | 2,2-diphenylvinyl |
| —COOH | hydrogen | 2-phenylethyl |
| —COOH | hydrogen | 2,2-diphenylethyl |
| —COOH | methyl | 2-phenylvinyl |
| —COOH | methyl | 2,2-diphenylvinyl |
| —COOH | methyl | 2-phenylethyl |
| —COOH | methyl | 2,2-diphenylethyl |
| —COOH | —CH₂COOH | 2-phenylvinyl |
| —COOH | —CH₂COOH | 2,2-diphenylvinyl |
| —COOH | —CH₂COOH | 2-phenylethyl |
| —COOH | —CH₂COOH | 2,2-diphenylethyl |
| —CONH₂ | hydrogen | 2-phenylvinyl |
| —CONH₂ | hydrogen | 2,2-diphenylvinyl |
| —CONH₂ | hydrogen | 2-phenylethyl |
| —CONH₂ | hydrogen | 2,2-diphenylethyl |
| —CH₂OH | hydrogen | 2-phenylvinyl |
| —CH₂OH | hydrogen | 2,2-diphenylvinyl |
| —CH₂OH | hydrogen | 2-phenylethyl |
| —CH₂OH | hydrogen | 2,2-diphenylethyl |

(Ie-1)

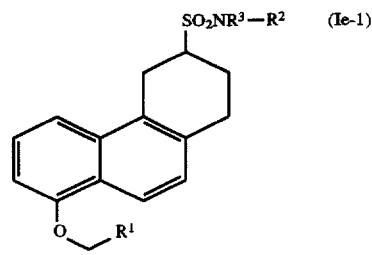

| R¹ | R³ | R² |
|---|---|---|
| —COOH | hydrogen | 2-phenylvinyl |
| —COOH | hydrogen | 2,2-diphenylvinyl |
| —COOH | hydrogen | 2-phenylethyl |
| —COOH | methyl | 2-phenylvinyl |
| —COOH | methyl | 2,2-diphenylvinyl |
| —COOH | methyl | 2-phenylethyl |
| —COOH | methyl | 2,2-diphenylethyl |
| —COOH | —CH₂COOH | 2-phenylvinyl |
| —COOH | —CH₂COOH | 2,2-diphenylvinyl |
| —COOH | —CH₂COOH | 2-phenylethyl |
| —COOH | —CH₂COOH | 2,2-diphenylethyl |
| —CONH₂ | hydrogen | 2-phenylvinyl |
| —CONH₂ | hydrogen | 2,2-diphenylvinyl |
| —CONH₂ | hydrogen | 2-phenylethyl |
| —CONH₂ | hydrogen | 2,2-diphenylethyl |

-continued

| R¹ | A | R³ | R² |
|---|---|---|---|
| —CH₂OH | | hydrogen | 2-phenylvinyl |
| —CH₂OH | | hydrogen | 2,2-diphenylvinyl |
| —CH₂OH | | hydrogen | 2-phenylethyl |
| —CH₂OH | | hydrogen | 2,2-diphenylethyl |

Salts

The compounds of the present invention of the formula (I) may be converted into the corresponding salts. Non-toxic and water-soluble salts are preferable. Suitable salts, for example, are follows: salts of alkaline metals (sodium, potassium etc.), salts of alkaline earth metals (calcium, magnesium etc.), ammonium salts, salts of pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.).

The compounds of the formula (I) may be converted into the corresponding acid addition salts. Non-toxic and water-soluble salts are preferable. Suitable salts, for example, are as follows: salts of inorganic acids e.g., hydrochloride, hydrobromide, hydroiode, sulfate, phosphate, nitrate; salts of organic acids e.g., acetate, lactate, tartarate, benzoate, citrate, methanesulphonate, ethanesulphonate, benzenesulphonate, toluenesulphonate, isedthioate, glucuronate, gluconate.

Process for the Preparation (1) The compound of the formula (Ia):

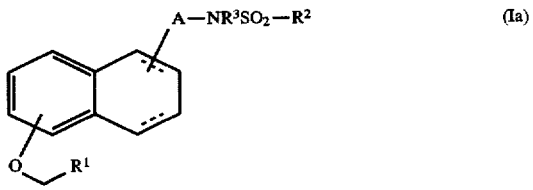

wherein all the symbols are the same meaning as hereinbefore defined, in the compounds of the formula (I), may be prepared:

(i) by subjecting a compound of the formula (II):

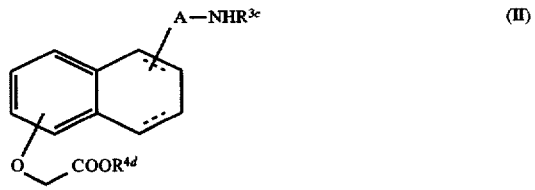

wherein $R^{3c}$ is hydrogen, C1–4 alkyl or —CH₂COOR$^{4a}$, R$^{4a}$ is C1–4 alkyl and the other symbols are the same meaning as hereinbefore defined, with a compound of the formula (III):

wherein $X^1$ is halogen and the other symbols are the same meaning as hereinbefore defined, to form an amide-bond, if necessary, followed by hydrolysis in an alkaline condition or forming an amide-bond or reduction, or (ii) by subjecting a compound of the formula (X):

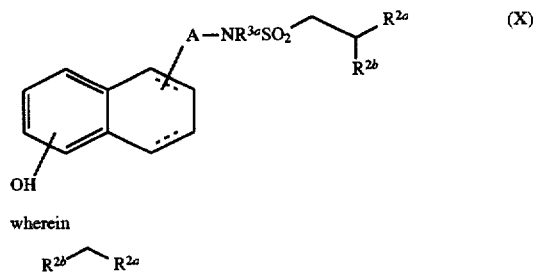

wherein $R^{2b}\diagdown R^{2a}$ is (i) C1–5 alkyl, C2–5 alkenyl or C3–5 alkynyl, (ii) C1–5 alkyl, C2–5 alkenyl or C3–5 alkynyl substituted by 1, 2, 3 of phenyl, C4–7 cycloalkyl or phenyl substituted by 1, 2 or 3 substituents of the following: C1–4 alkyl, C1–4 alkoxy or halogen or (iii) naphthyl, $R^{3a}$ is hydrogen or C1–4 alkyl, and the other symbols are the same meaning as hereinbefore defined, or a compound of the formula (XI):

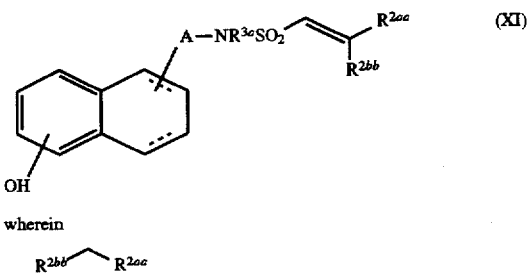

wherein $R^{2bb}\diagdown R^{2aa}$ is (i) C1–5 alkyl, (ii) C1–5 alkyl substituted by 1, 2 or 3 substituents of the following: phenyl, C4–7 cycloalkyl or phenyl substituted by 1, 2 or 3 substituents of the following: C1–4 alkyl, C1–4 alkoxy or halogen or (iii) naphthyl, and the other symbols are the same meaning as hereinbefore defined, with a compound of the formula (VI):

wherein $X^3$ is halogen and the other symbols have the same meaning as hereinbefore defined, to form an amide-bond, if necessary, followed by hydrolysis in an alkaline condition or forming an amide-bond or reduction.

(2) The compound of the formula (Ib):

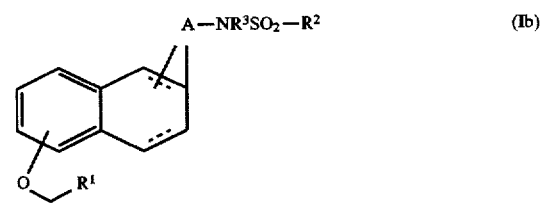

wherein all the symbols are the same meaning as hereinbefore defined, in the compounds of the formula (I), may be prepared by reacting a compound of the formula (XVI):

A—NR³ᶜSO₂—R² (XVI)

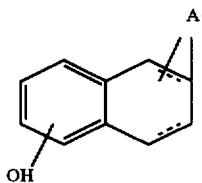

wherein all the symbols are the same meaning as hereinbefore defined, with a compound of the formula (VI):

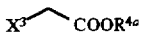
X³⌒COOR⁴ᵃ (VI)

wherein all the symbols are the same meaning as hereinbefore defined, if necessary, followed by hydrolysis in an alkaline condition or forming an amide-bond or reduction.

(3) The compound of the formula (Ic):

A—SO₂NR³—R² (Ic)

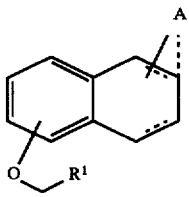

wherein all the symbols are the same meaning as hereinbefore defined, in the compounds of the formula (I), may be prepared:

(i) by subjecting a compound of the formula (XXIII):

A—SO₂X² (XXIII)

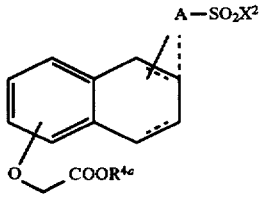

wherein X² is halogen and the other symbols are the same meaning as hereinbefore defined, with a compound of the formula (XXIV):

R³HN—R² (XXIV)

wherein all the symbols are the same meaning as hereinbefore defined, to form an amide-bond, if necessary, followed by hydrolysis in an alkaline condition or forming an amide-bond or reduction or (ii) by reacting a compound of the formula (XXVIII):

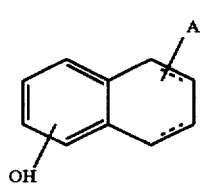

wherein A^b is bond or C1-2 alkylene, R^{8a} is hydrogen or C1-2 alkyl and the other symbols are the same meaning as hereinbefore defined, with a compound of the formula (VI):

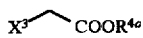
X³⌒COOR⁴ᵃ (VI)

wherein all the symbols are the same meaning as hereinbefore defined, to form an amide-bond, if necessary, followed by hydrolysis in an alkaline condition or forming an amide-bond or reduction.

(4) The compound of the formula (Ie):

A—SO₂NR³—R² (Ie)

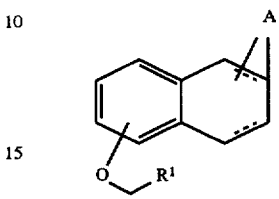

wherein all the symbols are the same meaning as hereinbefore defined, in the compounds of the formula (I), may be prepared by reacting a compound of the formula (XXXIII):

A—SO₂NR³ᵃ—R² (XXXIII)

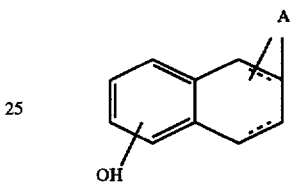

wherein all the symbols are the same meaning as hereinbefore defined, with a compound of the formula (VI):

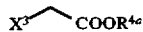
X³⌒COOR⁴ᵃ (VI)

wherein all the symbols are the same meaning as hereinbefore defined, if necessary, followed by hydrolysis in an alkaline condition or forming an amide-bond or reduction.

The reaction to form an amide-bond is known. For example, the reaction may be carried out in organic solvent (benzene, toluene, methylene chloride etc.), or in the absence of solvent, using a tertiary amine (pyridine, triethylamine etc.) at 0°–50° C., or it may be carried out in organic solvent (methylene chloride, tetrahydrofuran (THF), etc.), using a corresponding base, in the presence or absence of corresponding condensing agents (2-chloro-N-methylpyridinium iodide etc.) at 0°–40° C.

The hydrolysis of ester in an alkaline condition is known. For example, hydrolysis may be carried out in a water-miscible organic solvent (methanol, ethanol dimethoxyethane or mixture thereof etc.), using an alkali (sodium hydroxide, potassium hydroxide etc.), at 0°–50° C.

The reduction reaction is known. For example, the reduction may be carried out in organic solvent (methanol, ethanol, tetrahydrofuran, methylene chloride etc.), using lithium aluminum hydride or sodium boronium hydride at 0°–50° C.

The reactions of (1)-(ii), (2), (3)-(ii) and (4) are known. For example, the reaction may be carried out in organic solvent (dimethylformamide (DMF), acetone etc.), in the presence of potassium carbonate or sodium carbonate at 0°–160° C.

The compound of the formula (II), (X), (XI), (XVI), (XXIII), (XXVIII) and (XXXIII) may be prepared by using a reaction depicted in following scheme (A), (B), (C), (D), (E) and (F).

The symbols are the following or have the same meaning as hereinbefore defined.

Boc: t-butoxycarbonyl

Cbz: benzyloxycarbonyl
TMEDA: N, N, N', N'-tetramethylethylenediamine
X⁴: halogen
R³ᵇ: C1-4 alkyl
Aᵃ:
—(CH₂)m—C(=O)—(CH₂)n—
R⁸: C1-3 alkyl
R⁹: methyl, ethyl, methoxymethyl, tetrahydropyran
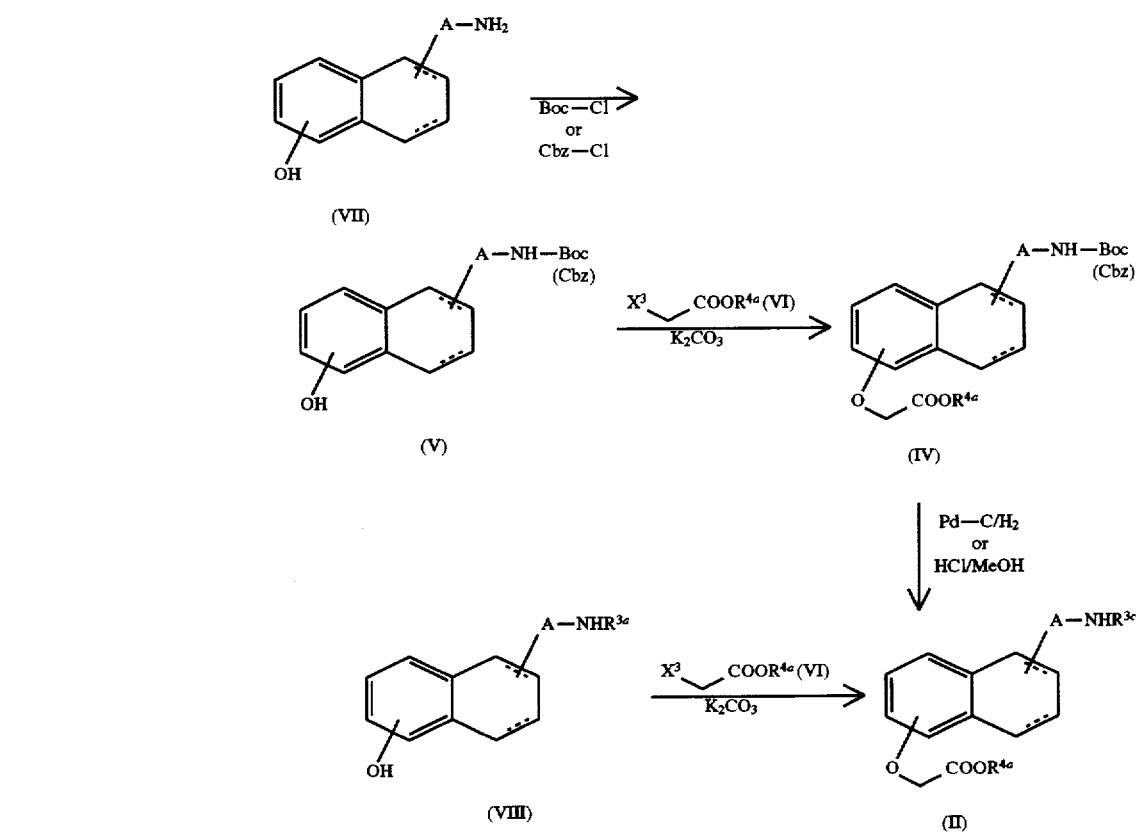
Scheme (A)

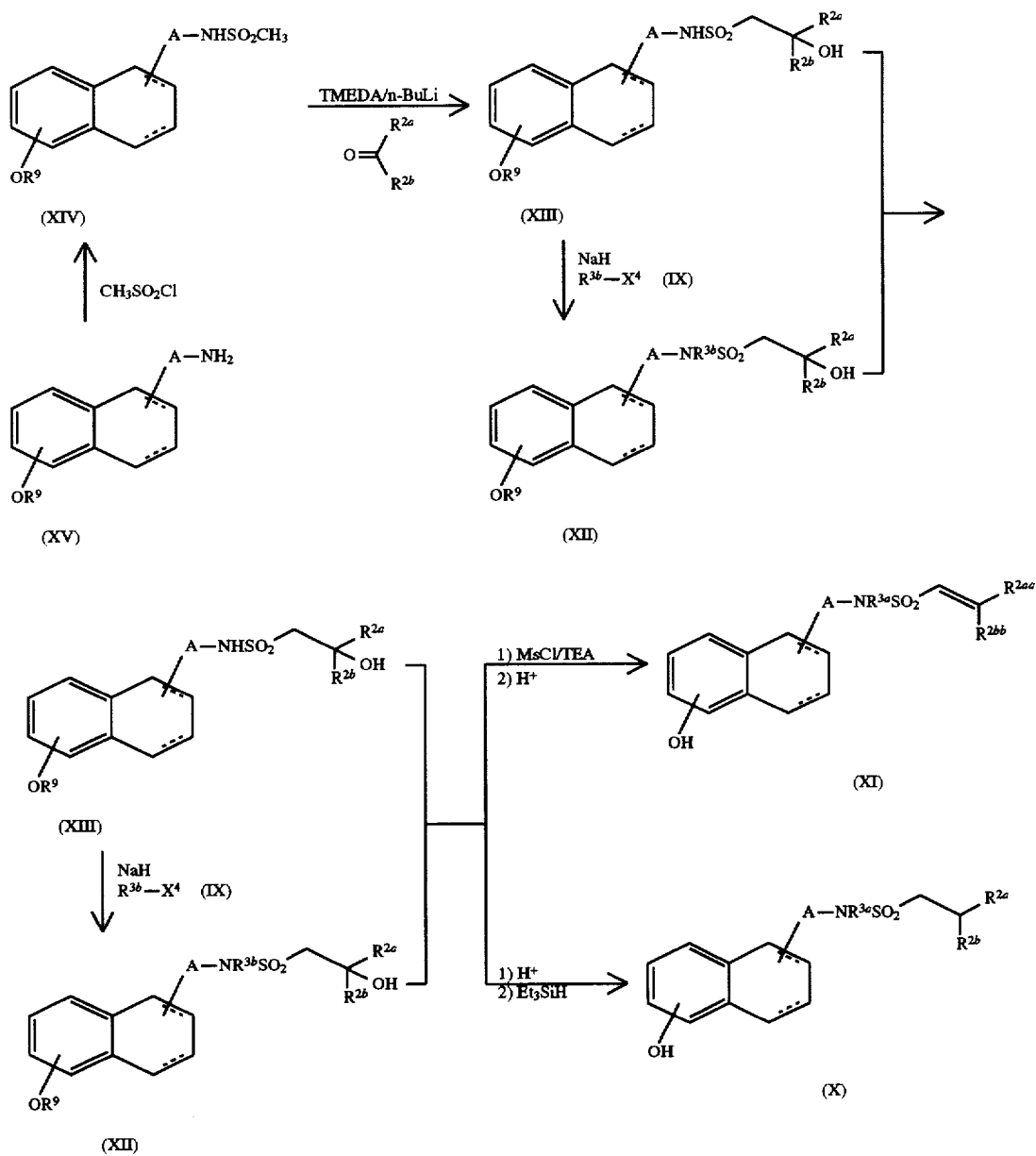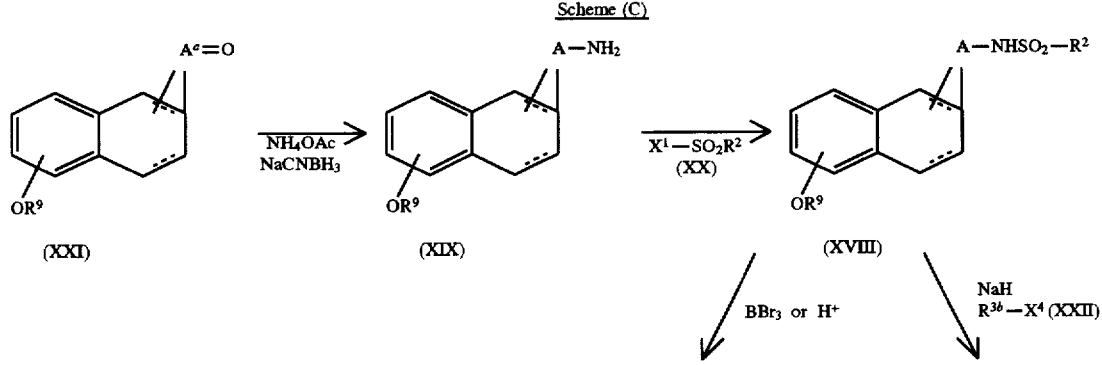

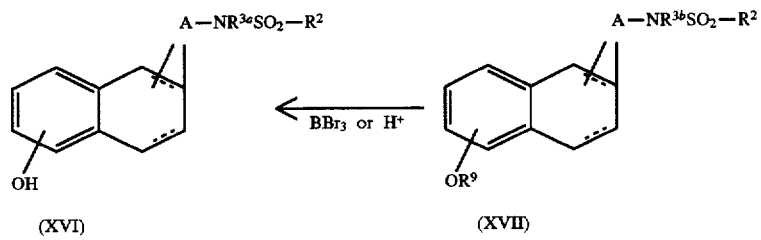
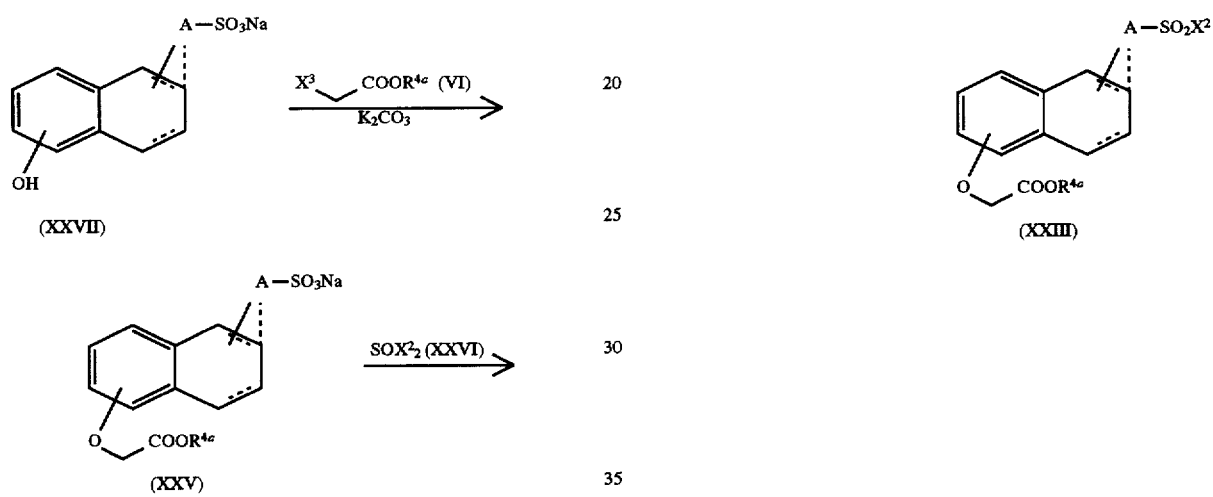
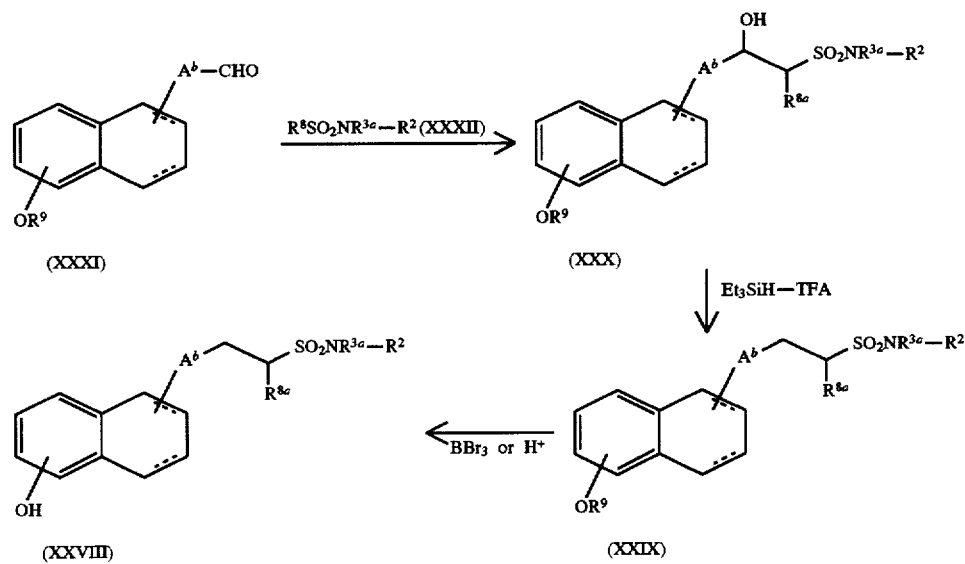

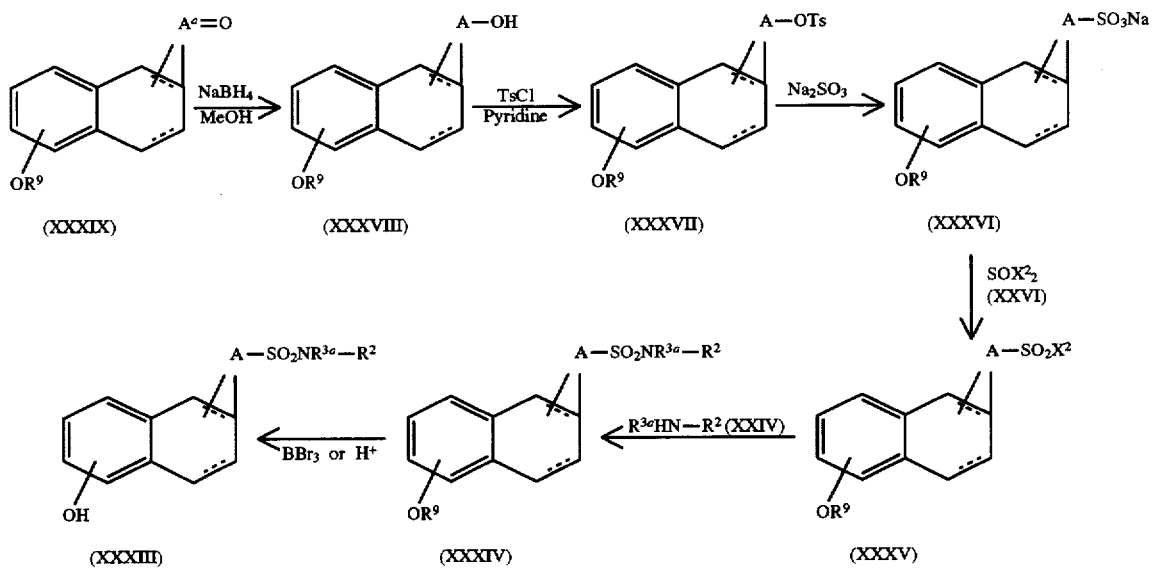

Scheme (F)

In each reaction in the present specification, products may be purified by conventional techniques. For example, purification may be carried out by distillation at atmospheric or reduced pressure, by high performance liquid chromatography, thin layer chromatography or by column chromatography using silica gel or magnesium silicate, by washing or by recrystallization. Purification may be carried out after each reaction, or after a series of reactions.

Starting materials and reagents

The starting materials and reagents in the present invention are known per se or may be prepared by known methods.

Pharmacological Activities

For example, in standard laboratory tests, the effects were confirmed by (i) binding assay using expression cell of prostanoide receptor subtype.

The compounds of the present invention of the formula (I) are useful for $PGE_2$ antagonists or agonists, because they bind to prostaglandin $E_2$ receptors and exhibit antagonist or agonist activity against the action thereof.

$PGE_2$ antagonists are expected to inhibit uterine contraction, to have analgesic action, to inhibit digestive peristalsis, to induce sleep, etc. Therefor, $PGE_2$ antagonists are considered to be useful for the prevention of abortion, pain, diarrhea, and insomnia.

$PGE_2$ agonists are expected to promote uterine contraction, to promote digestive peristalsis, to suppress a gastric acid secretion, to lower blood pressure. Therefor, $PGE_2$ agonists are considered to be useful for abortion, cathartics, antiulcer, anti-gastritis, antihypertensive.

(i) Binding assay using expression cell of prostanoide receptor subtype

The preparation of membrane fraction was carried out according to the method of Sugimoto et al [J. Biol. Chem. 267, 6463–6466 (1992)], using prostanoide receptor subtype (mouse $EP_{3\alpha}$).

The standard assay mixture containing a membrane fraction (0.5 mg/ml), [$^3$H]-$PGE_2$ in a final volume of 200 ml was incubated for 1 hour at room temperature. The reaction was terminated by the addition of 3 ml of ice-cooled buffer. The mixture was rapidly filtered through a Whatman GF/B glass filter. The radioactivity associated with the filter was measured in ACS II (Amarsham) by liquid scintillation counting.

Kd and Bmax values were determined from Scatchard plots [Ann. N.Y. Acad. Sci., 51, 660 (1949)]. Non-specific binding was calculated as the bond in the presence of an excess (2.5 mM) of unlabeled $PGE_2$. In the experiment for competition of specific [$^3$H]-$PGE_2$ binding by the compounds of the present invention, [$^3$H]-$PGE_2$ was added at a concentration of 2.5 nM and the compounds of the present invention were at a concentration of 1 mM.

The following buffer was used in all reactions.

Buffer: 10 mM potassium phosphate (pH 6.0), 1 mM EDTA, 10 mM $MgCl_2$, 0.1M NaCl The dissociation constant (Ki) of each compound was calculated by the following equation.

$Ki=IC_{50}/(1+([C]/Kd))$

Results were shown in table 1.

TABLE 1

| Ex. No. | Ki (µM) |
|---|---|
| 3 (g) | 0.007 |
| 3(h) | 0.037 |
| 3(i) | 0.037 |
| 3(p) | 0.036 |
| 3(q) | 0.32 |
| 3(v) | 0.017 |
| 3(w) | 0.028 |
| 3(aa) | 0.0079 |
| 3(ff) | 0.0025 |
| 6(f) | 0.0075 |

Toxicity

The toxicity of the compounds of the present invention of the formula (I) are very low and therefore safe for pharmaceutical use.

Application for Pharmaceuticals

The compounds of the present invention of the formula (I) and non-toxic salts thereof, are useful for $PGE_2$ antagonists or agonists, because they bind to prostaglandin $E_2$ receptors and have an activity of antagonist or agonist against the action thereof.

$PGE_2$ antagonists are considered to inhibit uterine contraction, to have an analgesic action, to inhibit digestive peristalsis, to induce sleep; therefore they are useful for prevention and/or treatment of abortion, pain, diarrhea, and insomnia.

PGE$_2$ agonists are considered to promote uterine contraction, to promote digestive peristalsis, to suppress a gastric acid secretion, to lower blood pressure and therefore are useful for the prevention and/or treatment of constipation, ulcers, gastritis, hypertensive, and for induction of labor in pregnant female mammals.

For the purposes above described, the compounds of the formula (I), of the present invention and non-toxic salts thereof may be normally administered systemically or locally, usually by oral or parenteral administration.

The doses to be administered are determined depending upon age, body weight, symptom, the desired therapeutic effect, the route of administration, and the duration of the treatment, etc. In the human adult, the doses per person per dose are generally between 1 μg and 100 mg, by oral administration up to several times per day, and between 0.1 μg and 10 mg, by parenteral administration up to several times per day. As mentioned above, the doses to be used depend upon various conditions. Therefore, there are cases in which doses lower than or greater than the ranges specified above may be used.

Solid compositions according to the present invention for oral administration include compressed tablets, dispersible powders and granules. In such solid compositions, one or more of the active compound(s) is or are, admixed with at least one inert diluent such as lactose, mannitol, glucose, hydroxypropylcellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, disintegrating agents such as cellulose calcium glycolate, stabilizing agent e.g. lactose and assistant for dissolving e.g. arginine, glutamic acid or aspartic acid. The tablets or pills may, if desired, be made into gastric film-coated or enteric film-coated tablets or pills, such as sugar-coated, gelatin-coated, hydroxypropyl cellulose-coated or hydroxypropylmethyl cellulose phthalate-coated tablets or pills; two or more layers may be used. The compositions for oral administration also include capsules of absorbable material such as gelatin.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavoring, perfuming and preserving agents.

Other compositions for oral administration include spray compositions which may be prepared by known methods and which comprise one or more of the active compound(s).

Preparations for injection according to the present invention for parenteral administration include sterile aqueous or non-aqueous solutions, suspensions or emulsions. Example of aqueous solvents or suspending media are distilled water for injection and physiological salt solution. Examples of non-aqueous solvents or suspending media are propylene glycol, polyethylene glycol, vegetable oils such as olive oil, alcohols such as ethanol, POLYSORBATE 80 (registered trademark). These compositions may also include adjuvants such as preserving, wetting, emulsifying, dispersing agents, stabilizing agents (e.g. lactose) and assisting agents for dissolving (e.g. arginine, glutamic acid or aspartic acid). They may also be manufactured in the form of sterile solid compositions which can be dissolved in sterile water or some other sterile injectable medium immediately before use.

Other compositions for parenteral administration include liquids for external use, and endermic liniments such as ointments, suppositories for rectal administration and pessaries for vaginal administration which comprise one or more of the active compound(s) and may be prepared by known methods.

REFERENCE EXAMPLES AND EXAMPLES

The following reference examples and examples illustrate the present invention, but do not limit the present invention.

The solvents in the parentheses show the developing or eluting solvents and the ratios of the solvents used are by volume in chromatographic separations.

Unless otherwise specified, "NMR" was measured in a chloroform-d (CDCl$_3$) solution.

Reference Example 1

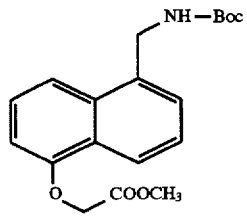

The mixture of 5-t-Butoxycarbonylaminomethyl-1-naphthol (940 mg), potassium carbonate (709 mg), methyl bromoacetate (0.44 ml) and acetone (15 ml) was stirred overnight at room temperature. To the reaction mixture, ethyl acetate was added. The mixture was filtered and the filtrate was concentrated. The residue was purified on silica gel chromatography to give the title compound (1.20 g) having the following physical data: mp: 109°–110° C.

NMR: δ8.34 (1 H, m), 7.67 (1 H, d), 7.50–7.36 (3H, m), 6.74 (1 H, d), 4.90–4.63 (5H, m), 3.82 (3H,s), 1.45 (9H,s).

Reference Example 2

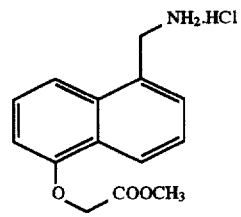

To a solution of the compound prepared in reference example 1 (200 mg) in methylene chloride (5 ml), 4N hydrochloric acid/ethyl acetate (5 ml) was added. The mixture was stirred for 1 hour at room temperature. The reaction mixture was concentrated to give the title compound.

Example 1

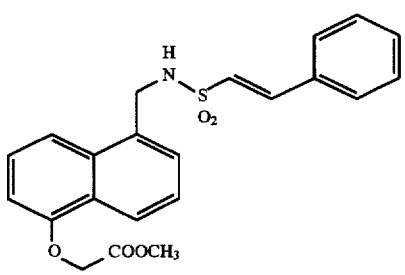

To the compound prepared in reference example 2 (150 mg), methylene chloride (10 ml), pyridine (0.24 ml), triethylamine (0.01 ml) and 2-phenylvinylsulphonylchloride (192 mg) was added. The mixture was stirred for 4 hours at room temperature. The reaction mixture was poured into water. The mixture was extracted with ethyl acetate. The organic layer was washed water and a saturated aqueous solution of sodium chloride, and dried over magnesium sulfate and concentrated. The residue was purified on silica gel chromatography to give the title compound (87 mg) having the following physical data. appearance: white solid mp: 117°–119° C.

NMR: δ 8.36(1H, d), 7.68(1H, d), 7.53–7.30(9H, m), 6.74(1H, d), 6.61(1H, d), 4.79(2H, s), 4.67(3H, s), 3.83(3H, s).

Reference Example 3

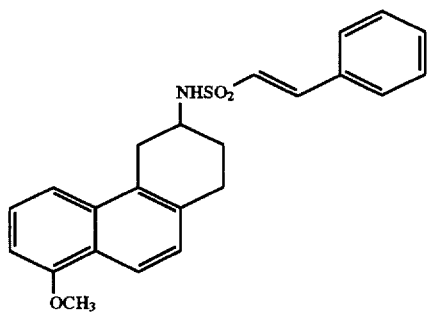

To a suspension of 6-keto-1-methoxy-5,6,7,8-tetrahydrophenanthrene (1.00 g) in methanol (30 ml), molecular sieves 4A (1 g), ammonium acetate (3.41 g) and sodium cyanoborohydride (292 mg) were added. The mixture was stirred for 5 hours at room temperature. The reaction mixture was filtered, and a filtrate was concentrated. To the residue was added an aqueous solution of sodium hydroxide. The mixture was extracted with ethyl acetate. The organic layer was dried over potassium carbonate, and concentrated. The residue was dissolved in ethyl acetate and 4N hydrochloric acid/ethyl acetate was added to it. The precipitated crystals were collected and dried, and 6-amine-1-methoxy-5,6,7,8-tetrahydrophenanthrene hydrochloride (1.0 g) was obtained.

To a solution of the above compound (500 mg) in methylene chloride (5 ml), triethylamine (1 ml) and β-styrylsulfonamide (606 mg) was added at 0° C. The mixture was stirred for 30 minutes at room temperature. The reaction mixture was poured into an aqueous solution of hydrochloric acid. The mixture was extracted with ethyl acetate. The organic layer was washed with water and a saturated aqueous solution of sodium chloride, and dried over and concentrated. The residue was purified by column chromatography on silica gel (hexane:ethyl acetate=3:1) to give the title compound (331 mg) having the following physical data: TLC: Rf 0.55 (hexane:ethyl acetate=1:1)

Reference Example 4

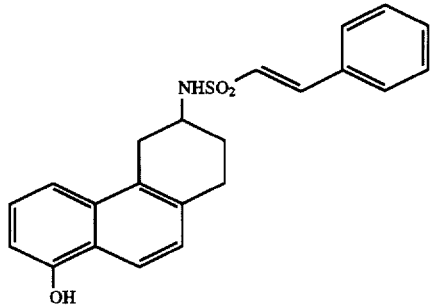

To a solution of the compound prepared in reference example 3 (300 mg) in methylene chloride (4 ml), a solution of boron tribromide (0.22 ml) in methylene chloride (2 ml) was added at −20° C. The mixture was stirred for 2 hours al −20°–0° C. The reaction mixture was poured into ice water, and extracted with ethyl acetate. The organic layer was washed with water and a saturated aqueous solution of sodium chloride, and dried over magnesium sulfate and concentrated. The residue was purified by column chromatography on silica gel (hexane:ethyl acetate=3:2) to give the title compound (282 mg) having the following physical data. TLC: Rf 0.39 (hexane:ethyl acetate=1:1 )

Example 2

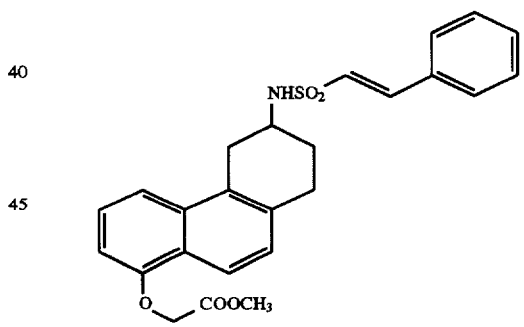

A solution of the compound prepared in reference example 4 (150 mg), methyl bromoacetate (0.056 ml), sodium carbonate (85 mg) in dimethylformamide (DMF; 3 ml) was stirred for 4.5 hours at 100° C. The reaction mixture was cooled and poured into water and extracted with ethyl acetate. The organic layer was washed with water and a saturated aqueous solution of sodium chloride, and dried over magnesium sulfate and concentrated. The residue was purified by column chromatography on silica gel (ethyl acetate:benzene=1:9) to give the title compound (142 mg) having the following physical data:

TLC: Rf 0.35 (15% ethyl acetate/benzene) NMR: δ 8.17 (1H, d), 7.85–7.16 (9H, m), 6.80 (1H, d), 6.68 (1H, d), 4.79 (2H, s), 4.58 (1H, d), 4.00–3.75 (4H, m), 3.49 (1H, dd), 3.10–2.93 (3H, m), 2.25–2.08 (1H, m), 2.03–1.80 (1H, m).

Reference Example 5

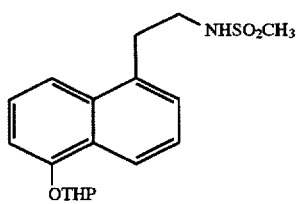

To a solution of 5-(2-aminoethyl)-1-tetrahydropyranyloxynaphthalene (3.0 g) in methylene chloride (15 ml), triethylamine (2.81 ml) and mesyl chloride (1.35 ml) was added at 0° C. The mixture was stirred for 1 hour at room temperature. The reaction mixture was poured into dil. hydrochloric acid. The mixture was extracted with ethyl acetate. The organic layer was washed with a saturated aqueous solution of sodium bicarbonate and a saturated aqueous solution of sodium chloride, and dried over magnesium sulfate and concentrated. The residue was purified by column chromatography on silica gel (ethyl acetate:hexane=1:2) to give the title compound (2.20 g) having the following physical data: TLC: Rf 0.42 (hexane:ethyl acetate=1:1)

Reference Example 6

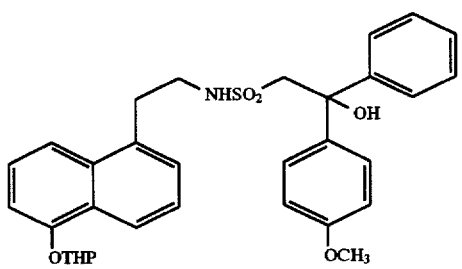

A solution of the compound prepared in reference example 5 (300 mg) in THF (5 ml), tetramethylethlenediamine (TMEDA; 0.26 ml) was added. The mixture was cooled at –60° C. under an atmosphere of argon. To the mixture, n-butyl lithium (1.66M in hexane; 1.60 ml) was dropped. The reaction mixture was warmed to –30° C. for 1.5 hours. The reaction mixture was recooled at –60° C. A solution of p-methoxybenzophenone (200 mg) in THF (3 ml) was added to the above mixture. The mixture was warmed to –30° C. with stirring. Water was poured into the reaction mixture. The mixture was extracted with ethyl acetate. The organic layer was washed with water and a saturated aqueous solution of sodium chloride, and dried over magnesium sulfate and concentrated. The residue was purified by column chromatography on silica gel (hexane:ethyl acetate=3:1) to give the title compound (253 mg) having the following physical data.

TLC: Rf 0.47 (hexane: ethyl acetate=1:1)

Reference Example 7

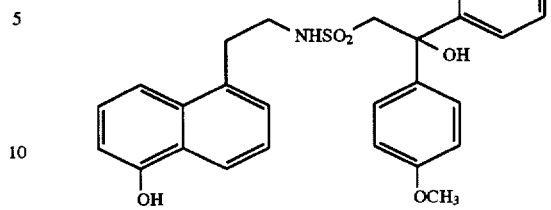

A solution of the compound prepared in reference example 6 (243 mg) in methanol (3 ml), pyridinium p-toluenesulfonic acid (PPTS; 30 mg) was added. The mixture was stirred overnight at room temperature. Methanol was distilled off, the residue was diluted with ethyl acetate. The organic layer was washed with water and a saturated aqueous solution of sodium chloride, and dried over magnesium sulfate and concentrated. The residue was purified by column chromatography on silica gel (hexane:ethyl acetate=3:2) to give the title compound (204 mg) having the following physical data.

TLC: Rf 0.16 (hexane: ethyl acetate=2:1)

Reference Example 8

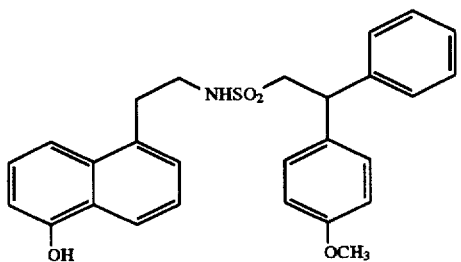

A solution of the compound prepared in reference example 7 (194 mg) in methylene chloride (2 ml), trifluoroacetic acid (TFA; 1 mg) and triethylsilane (0.20 ml) was added. The mixture was stirred overnight at room temperature. The reaction mixture was neutralized by adding a saturated aqueous solution of sodium bicarbonate, the mixture was extracted with ethyl acetate. The organic layer was washed with a saturated aqueous solution of sodium chloride, and dried over magnesium sulfate and concentrated. The residue was purified by column chromatography on silica gel (hexane:ethyl acetate=2:1) to give the title compound (162 mg) having the following physical data.

TLC: Rf 0.29 (hexane:ethyl acetate=1:1)

Reference Example 9

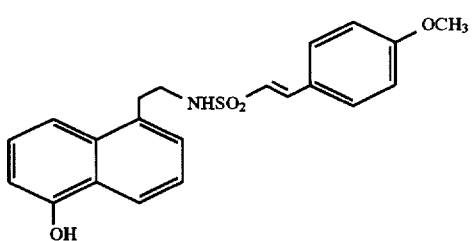

To a solution of the compound, 5-[2-[2-hydroxy-2-(4-methoxyphenyl) ethylsulfonylamino]ethyl]-1-tetrahydropyranyloxynaphthalene, prepared by the same procedure as the series of reactions of reference examples 5 and 6 (318 mg) using a corresponding compound in methylene chloride (3 ml), triethylamine (0.20 ml) and mesyl chloride (83 μl) was added at 0° C. The mixture was stirred for 2 hours at room temperature. To the reaction mixture, a saturated aqueous solution of sodium bicarbonate was added. The mixture was extracted with ethyl acetate. The organic layer was dried over sodium sulfate and concentrated. The residue was dissolved into methanol, and 2N aqueous solution of hydrochloric acid was added to the above mixture. The mixture was stirred for 12 hours at room temperature. The reaction mixture was concentrated. Water was added to the residue, the mixture was extracted with ethyl acetate. The organic layer was washed a saturated aqueous solution of sodium bicarbonate, and dried over magnesium sulfate and concentrated. The reside was purified by column chromatography on silica gel (hexane:ethyl acetate=2:1) to give the title compound (65 mg) having the following physical data.

TLC: Rf 0.54 (hexane:ethyl acetate=1:1)

Example 3

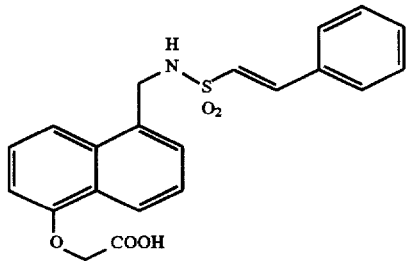

To a solution of the compound prepared in example 1 (84 mg) in dimethoxyethane-methanol (2:1, 3 ml), 1N aqueous solution of sodium hydroxide (0.5 ml) was added. The mixture was stirred for 1 hour at room temperature. To the reaction mixture, 1N hydrochloric acid was added and the mixture was extracted with ethyl acetate. The organic layer was washed with a saturated aqueous solution of sodium chloride, and dried over magnesium sulfate and concentrated. The residue was recrystallized from ethyl acetate-hexane to give the title compound (82 mg) having the following physical data: appearance: white powder mp: 201°–204° C.

NMR (DMSO-d6): δ 8.18 (1H, d), 7.88(1H, t), 7.73 (1H, d), 7.68–7.30 (9H, m), 7.19 (1H, d), 6.92 (1H, d), 4.86 (2H, s), 4.52 (2H, d).

Example 3(a)–3(ee)

The compounds having the following physical data were obtained by the same procedure as the series of reactions of Reference example 1→Reference example 2→Example 1→Example 3 or Reference example 1→Example 1→Example 3.

Example 3(a)

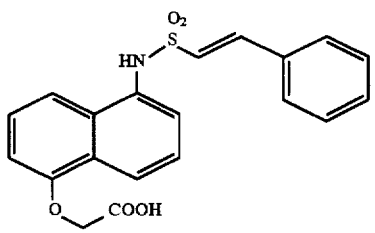

appearance: milk-white powder mp: 218.5°–219.5° C.

NMR (DMSO-d6): δ 13.03(1H,brs), 9.95(1H,s), 8.13(1H, dd), 7.84(1H,d), 7.70–7.20(10H,m), 6.87(1H,d), 4.85(2H,s).

Example 3(b)

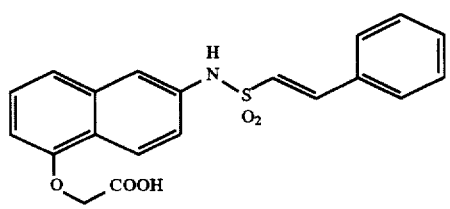

appearance: white powder mp: 180°–181° C.

NMR (DMSO-d6): δ 13.05(1H,brs), 10.34(1H,s), 8.12 (1H,d), 7.76–7.25(11H,m), 6.76(1H,d), 4.83(2H,s).

Example 3(c)

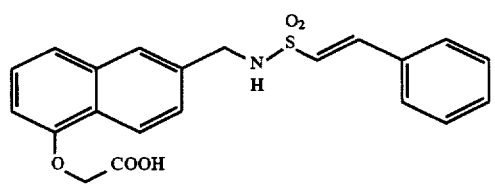

appearance: white powder mp: 177°–179° C.

NMR (DMSO-d6): δ 13.08(1H,brs), 8.18(1H,d), 7.97(1H, t), 7.80(1H,s), 7.67–7.28(9H,m), 7.13(1H,d), 6.84(1H,d), 4.84(2H,s), 4.28(2H,d).

Example 3(d)

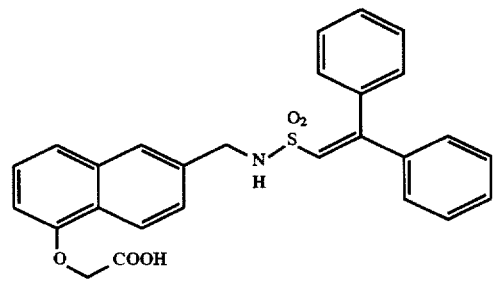

appearance: white powder mp: 211.8°–212.9° C.

NMR (DMSO-d6): δ 8.22(1H,d), 7.87(1H,t), 7.81(1H,s), 7.60–7.10(11H,m), 7.00–6.80(3H,m), 6.69(1H,s), 4.87(2H,s), 4.28(2H,d).

Example 3(e)

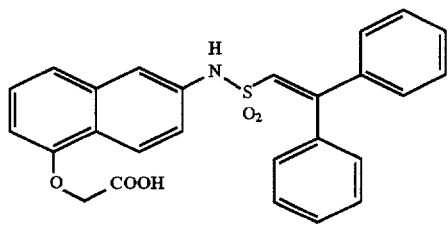

appearance: white powder

TLC: Rf 0.24 (methanol:methylene chloride=1:5) NMR (DMSO-d6): δ 10.12(1H,s), 8.13(1H,d), 7.50(1H,s), 7.48–7.20(9H,m), 7.10(2H,d), 7.02(2H,d), 6.97(1H,s), 6.77 (1H,m), 4.84(2H,s).

Example 3(f)

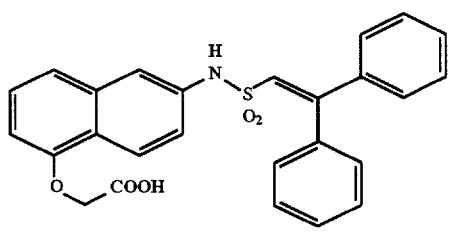

appearance: white powder mp: 142°–143° C.

NMR (DMSO-d6): δ 8.22(1H,d), 7.77(1H,t), 7.72(1H,d), 7.59–7.10(12H,m), 7.02(1H,d), 6.94(1H,d), 6.76(1H,s), 4.88(2H,s), 4.54(2H,d).

Example 3(g)

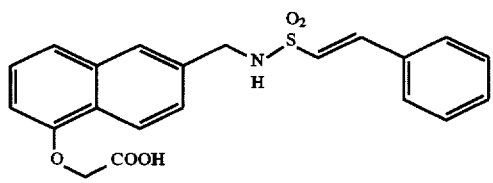

appearance: white powder mp: 182°–184° C.

NMR (CDCl3+CD3OD): δ 8.26(1H,m), 7.64(1H,d), 7.47–7.27(9H,m), 6.74(1H,d), 6.63(1H,d), 4.77(2H,s), 3.34–3.18(4H,m).

Example 3(h)

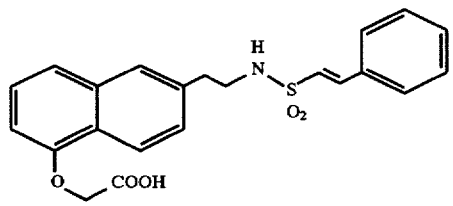

appearance: white powder mp: 139°–141° C.

NMR (CDCl3+H2O): δ 8.25(1H,d), 7.62(1H,s), 7.42–7.24 (9H,m), 6.64(1H,d), 6.61(1H,d), 4.80(2H,s), 3.38(2H,t), 3.01(2H,t).

Example 3(i)

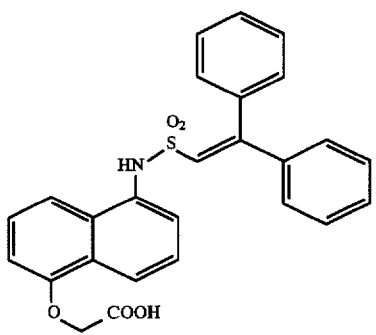

appearance: pale yellow powder mp: 200°–202° C.

NMR (DMSO-d6): δ 13.08(1H,brs), 9.93(1H,s), 8.19(1H, dd), 7.86(1H,d), 7.56–7.14(15H,m), 7.12–7.00(2H,m), 6.97–6.75(4H,m), 4.89(2H,s).

Example 3(j)

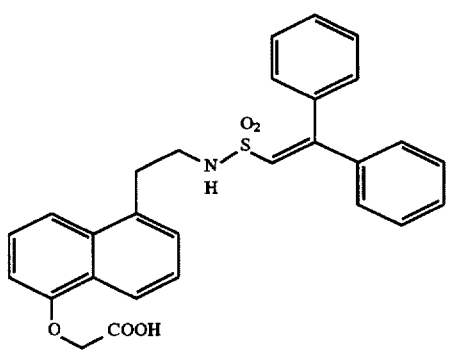

appearance: white powder mp: 158°–161° C.

NMR (DMSO-d6+CDCl3): δ 8.17(1H,m), 7.61(1H,d), 7.46–7.08(13H,m), 6.84(1H,d), 6.76(1H,s), 4.89(2H,s), 3.22 (4H,s like).

Example 3(k)

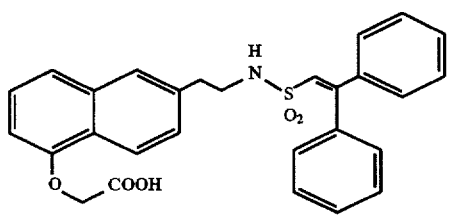

appearance: pale yellow powder mp: 149°–151° C.

NMR (DMSO-d6+CDCl3): δ 8.17(1H,d), 7.66(1H,s), 7.50–7.08(13H,m), 6.84–6.73(2H,m), 4.82(2H,s), 3.26(2H, m), 2.92(2H,t).

Example 3(l)

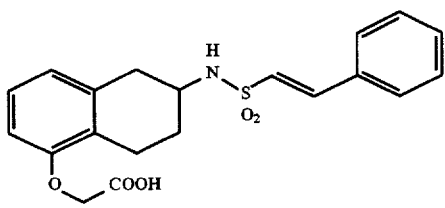

appearance: white powder mp: 180.5°–181.5° C.

NMR (CDCl$_3$+CD$_3$OD): δ 7.60–7.33(6H,m), 7.05(1H,t), 6.82(1H,d), 6.69(1H,d), 6.57(1H,d), 4.61 (2H,s), 3.75–3.60 (1H,m), 3.15–2.60(4H,m), 2.20–2.00(1H,m), 1.95–1.70(1H,m).

Example 3(m)

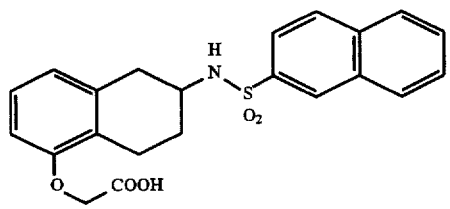

appearance: white powder mp: 164.6°–166.0° C.

NMR (CDCl$_3$+CD$_3$OD): δ 8.45(1H,s), 8.03–7.80(4H,m), ), 7.72–7.55(2H,m), 7.00(1H,t), 6.56(1H,d), 6.53(1H,d), 4.58(2H,s), 3.75–3.53(1H,m), 3.00–2.76(2H,m), 2.75–2.50 (2H,m), 2.00–1.80(1 H,m), 1.80–1.55(1 H,m).

Example 3(n)

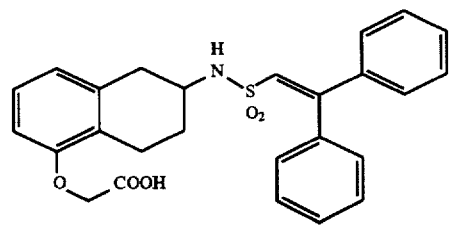

appearance: colorless amorphous

NMR: δ 7.50–7.20(10H,m), 7.05(1H,t), 6.87(1H,s), 6.65 (1H,d), 6.55(1H,d), 4.65(2H,s), 4.20–3.20(1H,br), 4.03(1H, d), 3.59(1H,m), 3.02–2.40(4H,m), 2.13–1.74(1H,m), 1.74–1.50(1H,m).

Example 3(o)

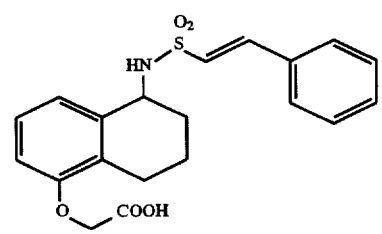

appearance: white powder mp: 210.7°–211.5° C.

NMR (CDCl$_3$+CD$_3$OD) δ 7.60–7.40(6H,m), 7.17–7.00 (2H,m), 6.90(1H,d), 6.62(1H,dd), 4.62(2H,s), 4.50(1H,t), 2.90–2.55(2H,m), 2.10–1.70(4H,m).

Example 3(p)

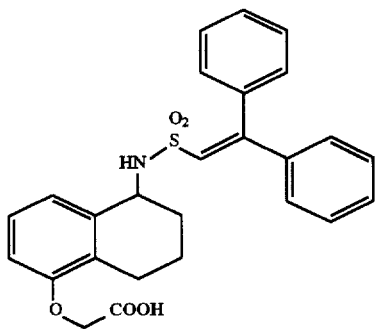

appearance: white powder mp: 184.5°–185.3° C.

NMR (CDCl$_3$+CD$_3$OD): δ 7.53–7.20(10 H,m), 7.20–7.00 (2H,m), 6.90(1H,s), 6.62(1H,d), 4.62(3H,m), 2.88–2.48(2H, m), 2.10–1.50(4H,m).

Example 3(q)

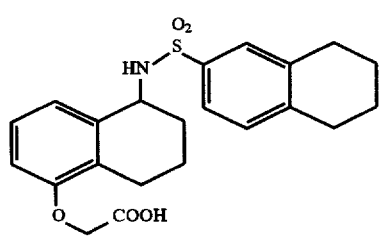

appearance: white powder mp: 230.8°–231.2° C.

NMR (CDCl$_3$+CD$_3$OD): δ 8.50(1H,s), 8.05–7.85(4H,m), 7.74–7.58(2H,m), 6.95(1H,t), 6.61 (1H,d), 6.56(1H,d), 4.57 (2H,s), 4.47(1H,m), 2.88–2.67(1H,m), 2.67–2.40(1H,m), 2.00–1.60(4H,m).

Example 3(r)

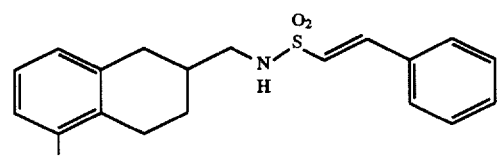

appearance: white powder mp: 159°–160° C.

NMR: δ 7.45(6H,m), 7.05(1H,t), 6.75(1H,d), 6.73(1H,d), 6.55(1H,d), 4.67(1H,s).

Example 3(s)

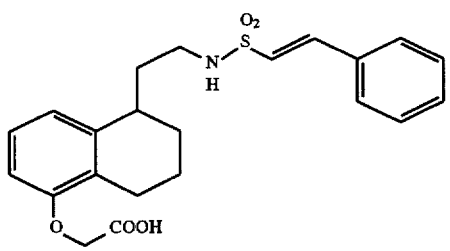

appearance: white powder m.p.: 101.0°–103.0° C.

NMR: δ 7.55–7.32(6H,m), 6.99(1H,d), 6.81–6.68(2H,m), 6.52(1H,d), 5.00(1H,brs),4.63(2H,s), 3.15(2H,m), 2.95–2.51 (4H,m), 2.06–1.53(6H,m).

Example 3(t)

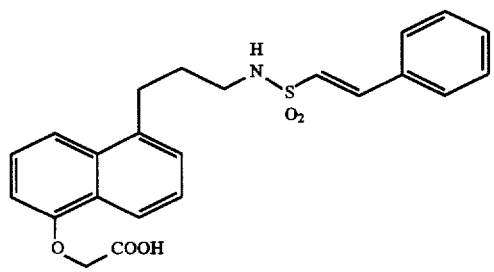

TLC: 0.30 (methanol:methylene chloride=1:5) NMR (CDCl$_3$+CD$_3$OD): δ 8.12 (1H, dd), 7.47 (1H, d), 7.40–7.10 (9H, m), 6.63 (1H, d), 6.60 (1H, d), 4.65 (2H, s), 2.97 (4H, m), 1.87 (2H, m).

Example 3(u)

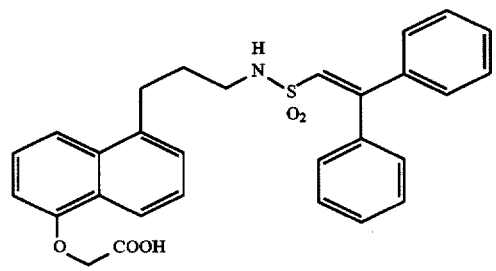

TLC: Rf 0.30 (methanol:methylene chloride=1:4) NMR (CDCl$_3$+CD$_3$OD): δ 8.25 (1H, d), 7.60–7.15 (14H, m), 6.78 (1H, s), 6.75 (1 H, d), 4.78 (2H, s), 3.05–2.82 (4H, m), 1.73 (2H, m).

Example 3(v)

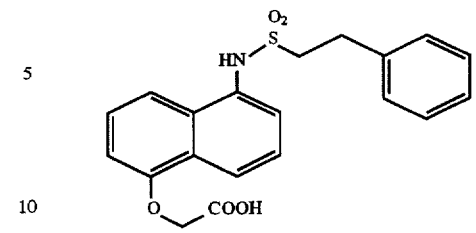

TLC: Rf 0.26 (30% methanol/chloroform) NMR (CD$_3$OD:CDCl$_3$=2:1): δ 8.33 (1 H, d), 7.88 (1 H, d), 7.64 (1 H, d), 7.54–7.42 (2 H, m), 7.30–7.03 (5 H, m), 6.87 (1 H, d), 4.-83 (2 H, s), 3.40–3.27 (2 H, m), 3.18–3.05 (2 H, m).

Example 3(w)

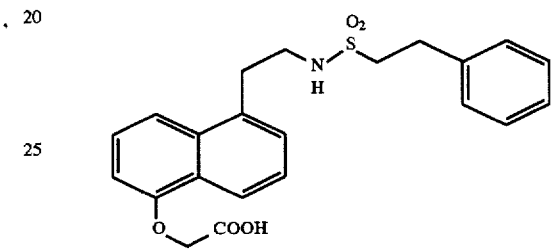

TLC: Rf 0.29 (30% methanol chloroform) NMR (CDCl$_3$: CD$_3$OD=1:2) δ 8.31 (1 H, m), 7.71 (1 H, d), 7.52–7.06 (8 H, m), 6.81 (1 H, d), 4.80 (2 H, s) 3.48–3.22 (4 H, m), 3.17–2.89 (4 H, m).

Example 3(x)

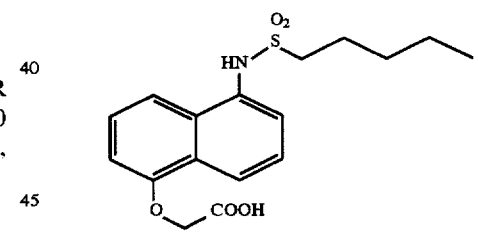

TLC: Rf 0.26 (30% methanol/chloroform) NMR (CD$_3$OD:CDCl$_3$=2:1): δ 8.33 (1 H, d), 7.84 (1 H, d), 7.62 (1 H, d), 7.53–7.40 (2 H, m), 6.87 (1 H, d), 4.84 (2 H, s), 3.14–3.02 (2 H, m), 1.93–1.74 (2 H, m), 1.42–1.16 (4 H, m), 0.85 (3 H, t).

Example 3(y)

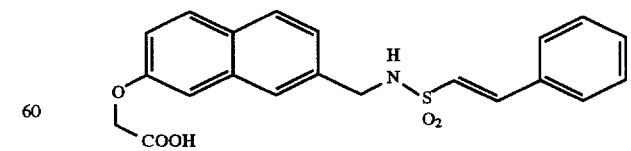

TLC: Rf 0.19 (25% methanol/chloroform) NMR (DMSO-d6): δ 13.02 (1 H, brs), 7.93 (1 H, t), 7.83–7.68 (3 H, m), 7.63–7.51 (2 H, m), 7.43–7.04 (8 H, m), 4.77 (2 H, s), 4.26 (2 H, d).

Example 3(z)

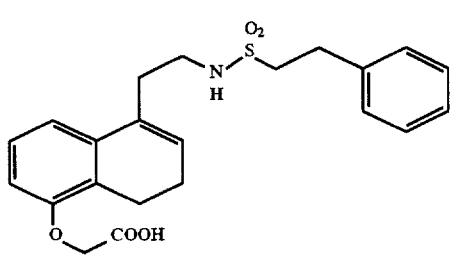

TLC: Rf 0.32 (30% methanol/chloroform) NMR: δ 7.33–7.07 (6 H, m), 6.88 (1 H, d,), 6.68 (1 H, d), 5.94 (1 H, 7), 5.00–4.00 (1 H, br s), 4.65 (2 H, s), 4.32 (1 H, t), 3.28–2.95 (4 H, m), 2.80 (2 H, t), 2.65 (2 H, t), 2.22 (2 H, m).

Example 3(aa)

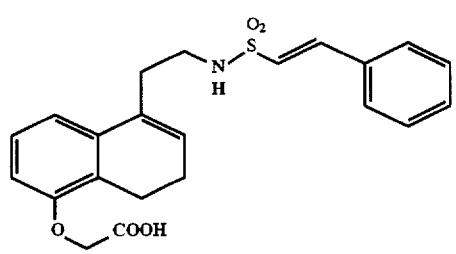

TLC: Rf 0.29 (30% methanol/chloroform) NMR (CDCl$_3$:CD$_3$OD=1:2): δ 7.54–7.30 (6 H, m), 7.04 (1 H, t), 6.91 (1 H, d), 6.80 (1 H, d), 6.67 (1 H, d), 5.95 (1 H, t), 4.60 (2 H, s), 3.15 (2 H, t), 2.84–2.63 (4 H, m), 2.19 (2 H, m).

Example 3(bb)

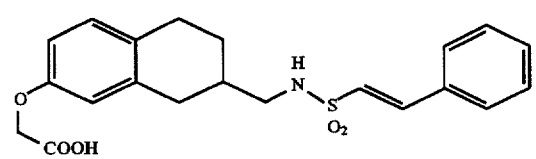

TLC: Rf 0.24 (30% methanol/chloroform) NMR (DMSO-d6): δ 12.90 (1 H, br s), 7.87–7.64 (2 H, m), 7.49–7.26 (5 H, m), 7.19 (1 H, d), 6.94 (1 H, d), 6.67–6.55 (2 H, m), 4.55 (2 H, s), 2.95–2.27 (6 H, m), 2.00–1.74 (2 H, m), 1.44–1.20 (1 H, m).

Example 3(cc)

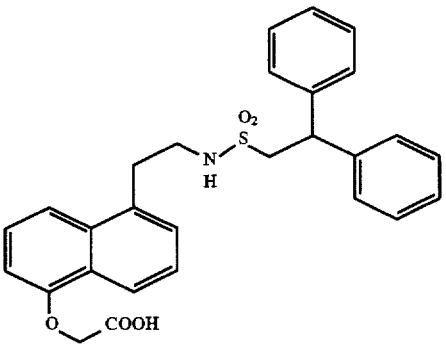

TLC: Rf 0.29 (chloroform:methanol=5:1) NMR (CDCl$_3$+CD$_3$OD): δ 8.094 (1 H, d), 7.28–7.03 (14H, m), 6.58 (1 H, d), 4.50 (1 H, t), 4.45 (2H, s), 3.64 (2H, d), 2.89–2.85 (2H, m), 2.79–2.75 (2 H, m).

Example 3(dd)

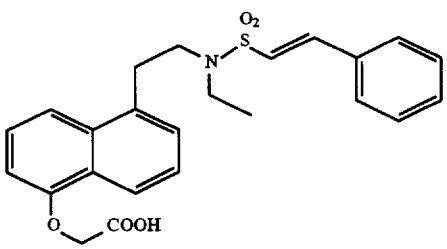

TLC: Rf 0.50 (chloroform:methanol:acetic acid=19:1:0.1) NMR (DMSO-d6): δ 8.16 (1H, dd), 7.75–7.66 (3H, m), 7.50–7.35 (7H, m), 7.25 (1 H, d), 6.89 (1 H, d), 4.87 (2H, s), 3.60–3.30 (4H, m), 3.28 (2H, q), 1.14 (3H, t).

Example 3(ee)

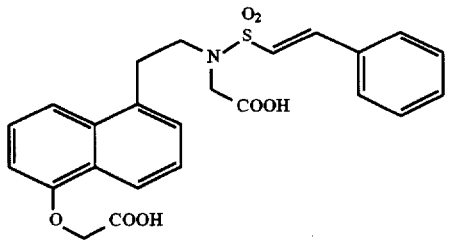

TLC: Rf 0.08 (chloroform:methanol=5:1) NMR (CD$_3$OD): δ 8.28–8.22 (1H, m), 7.22 (1H, d), 7.50 2 (9H, m), 6.84 (1H, d), 6.79 (1 H, d), 4.80 (2H, s), 4.07 (2H, s), 3.60–3.51 (2H, m), 3.44–3.35 (2H, m).

45
Example 3(ff)

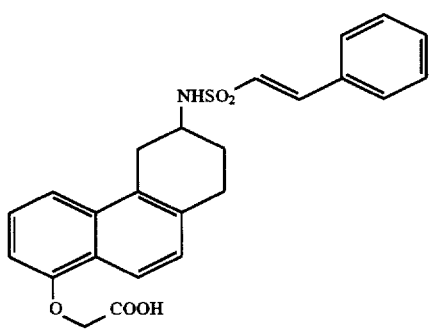

The title compound having the following physical data was obtained by the same procedure of Example 3, using the compound prepared in Example 2.

TLC: Rf 0.21 (30% methanol/chloroform) NMR (DMSO-d6): δ 12.96 (1 H, br s), 8.04 (1 H, d), 7.75–7.55 (3 H, m), 7.50–7.15 (8 H, m), 6.81 (1 H, d), 4.81 (2 H, s),3.78–3.30 (2 H, m), 3.07–2.81 (3 H, m), 2.21–2.03 (1 H, m), 1.94–1.68 (1 H, m).

Example 3(gg)–3(ll)

The compounds having the following physical data were obtained by the same procedure as the series of reactions of Example 2→Example 3, using the compound prepared in Reference example 8 or Reference example 9, or by the same procedure as the series of reactions of Reference example 5→Reference example 6→Reference example 7→Reference example 8→Example 2→Example 3 or Reference example 5→Reference example 6→Reference example 9→Example 2→Example 3 using corresponding compounds.

Example 3(gg)

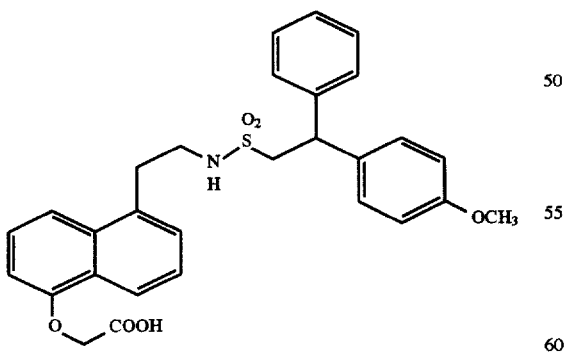

TLC: Rf 0.30 (25% methanol/chloroform) NMR (DMSO-d6): δ 8.17 (1H, d), 7.59–7.05 (11H, m), 6.91–6.72 (3H, m), 4.72 (2H, s), 4.37 (1H, t), 4.20–3.20 (7H, m), 3.15–3.00 (4H, m).

46
Example 3(hh)

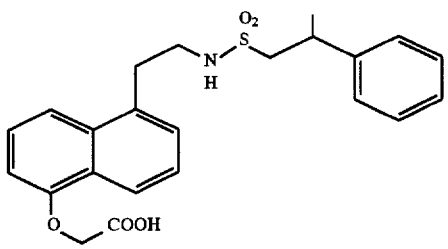

TLC: Rf 0.26 (25% methanol/chloroform) NMR (DMSO-d6): δ 8.16 (1 H, m), 7.70–7.11 (9H, m), 6.89 (1 H, d), 4.86 (2H, s), 3.80–2.90 (9H, m), 1.50 (3H, d).

Example 3(ii)

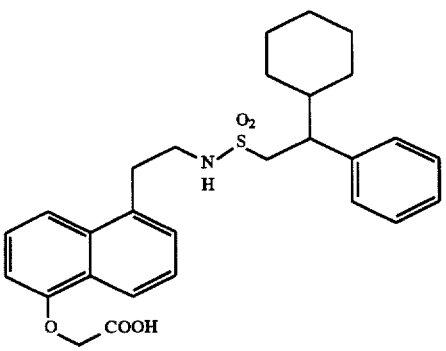

TLC: Rf 0.32 (25% methanol/chloroform) NMR (DMSO-d6): δ 8.18 (1 H, d), 7.60–6.80 (11H, m), 4.88 (2H, s), 3.60–2.80 (8H, m), 2.00–0.50 (1 1 H, m).

Example 3(jj)

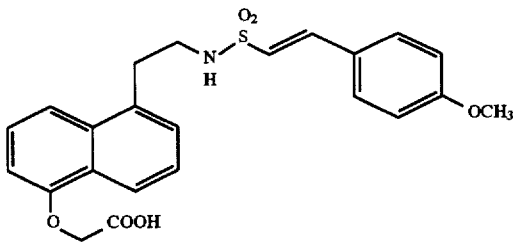

TLC: Rf 0.38 (chloroform:methanol:acetic acid= 19:1:0.1) NMR (DMSO-d6): δ 8.20–8.10 (1 H, m), 7.68–7.57 (3H, m), 7.48–7.25 (5H, m), 7.00–6.83 (4H, m), 4.85 (2H, s), 3.79 (3H, s), 3.50–3.10 (4H, m).

Example 3(kk)

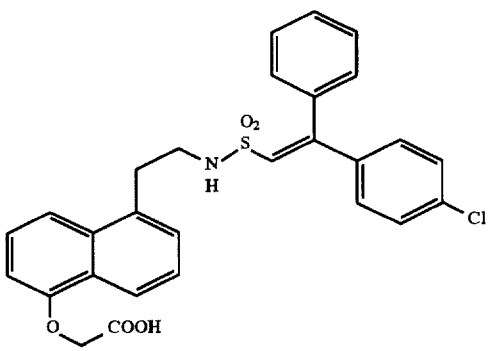

TLC: Rf 0.49 (chloroform:methanol:acetic acid= 19:1:0.1) NMR (DMSO-d6): δ 8.20–8.10 (1H, m), 7.62–7.52 (1H, m), 7.50–7.08 (13H, m), 6.90–6.78 (2H, m), 4.70 (2H, s), 3.30–3.10 (4H, m).

Example 3(ll)

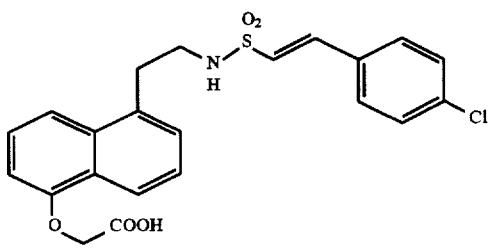

TLC: Rf 0.25 (chloroform:methanol=3:1) NMR: δ 8.33–8.26 (1 H, m), 7.57 (1 H, d), 7.45–7.20 (8H, m), 6.99 (1 H, d), 6.37 (1H, d), 4.77 (2H, s), 4.60–4.50 (1 H, br), 3.52–3.28 (4H, m).

Reference Example 10

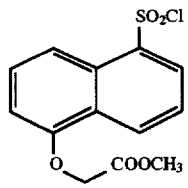

To a solution of sodium 5-hydroxynaphthalenesulphonate (10 g) in dimethylformamide (50 ml), sodium carbonate (6.46 g) and methyl bromoacelate (9.32 g) were added. The mixture was stirred for 10 hours at 100° C. The reaction mixture was filtered and the filtrate was concentrated. To a solution of the residue in dimethylformamide (50 ml), thionylchloride (9.67 g) was added at 0° C. The mixture was stirred for 30 minutes at 0° C. To the reaction mixture, water was added and filtered. The residue was washed with hexane and dried over to give the title compound having the following physical data.

TLC: Rf 0.17 (ethyl acetate:hexane=1:5) NMR: δ 8.83 (1H, d), 8.46–8.35 (2H, m), 7.68 (1H, t), 7.62 (1H, t), 6.92 (1H, d), 4.87 (2H, s), 3.84 (3H, s).

Example 4

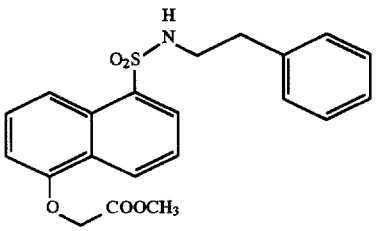

To the compound prepared in reference example 10 (0.315 g) in methylene chloride (5 ml), a solution of 2-phenylethylamine (0.158 g) in methylene chloride (10 ml) and triethylamine (0.395 g) was dropped. The mixture was stirred for 4 hours at room temperature. Water was poured into the reaction mixture. The mixture was extracted with ethyl acetate. The organic layer was washed 1N hydrochloric acid and water, and dried over sodium sulfate and concentrated. The residue was recrystallized from ethyl acetate-hexane to give the title compound (0.279 mg) having the following physical data. appearance: pale yellow powder top: 97.5°–98.5° C.

NMR: δ 8.67 (1H, d), 8.27 (1H, d), 8.12 (1H, d), 7.56 (1H, t), 7.47 (1H, t), 7.20–7.10 (3H, m), 6.96–6.87 (2H, m), 6.81 (1 H, d), 4.87 (2H, s), 4.55 (1H, t), 3.84 (3H, s), 3.17 (2H, dt), 2.65 (2H, t).

Reference Example 11

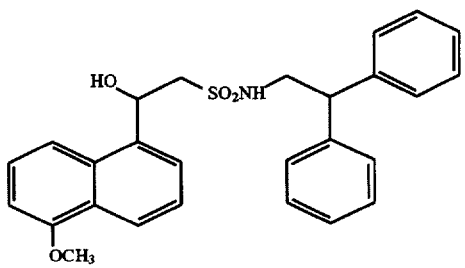

To a solution of N-(2,2-diphenylethyl) methanesulfoneamide (5.51 g) in THF (60 ml) and TMEDA (12.1 ml), n-butyl lithium (1.66M in hexane; 24.1 ml) was dropped at −78° C. The mixture was stirred to warm up to −20° C. for 2.5 hours, and was recooled to −70° C. A solution of the 5-aldehyde-1-methoxynaphthalene (3.72 g) in THF (20 ml) was slowly added to the above solution at −50 ° C. The mixture was stirred to warm up to −15 ° C. To the reaction mixture, 1N aqueous solution of hydrochloric acid was added, and then the mixture was extracted with ethyl acetate. The organic layer was washed with water, a saturated aqueous solution of sodium chloride, dried over magnesium sulfate and concentrated to give the title compound (6.64 g) having following physical data.

TLC: Rf 0.37 (ethyl acetate:hexane=1:2); NMR: δ 8.29 (1 H, d.), 7.70 (1 H, d), 7.54–7.38 (3 H, m), 7.38–7.13 (10 H, m), 6.84 (1 H, d), 5.95 (1 H, m), 4.45 (1 H, t), 4.19 (1 H, t), 4.00 (3 H, s), 3.74 (2H, t), 3.42–3.23 (2 H, m).

Reference Example 12

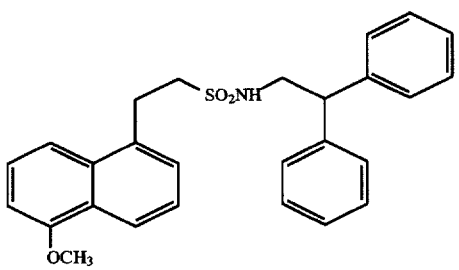

To a solution of the compound prepared in reference example 11 (130 g) in methylene chloride (870 ml) and TFA (271 ml), triethylsilane (81.9 g) was added at room temperature. The mixture was stirred for 15 hours at room temperature. The reaction mixture was concentrated. The residue was dissolved with ethyl acetate and the solution was filtered to remove the white precipitate. The filtrate was concentrated. The residue was purified by the column chromatography (ethyl acetate:hexane=1:6→1:3) to give the title compound (95.1 g) having following physical data.

TLC: Rf 0.43 (ethyl acetate:hexane=1:2); NMR: δ 8.23 (1 H, d), 7.55–7.10 (15 H, m), 6.85 (1 H, d), 4.08–3.93 (4 H, m), 3.58 (2 H, dd), 3.53–3.37 (2 H, m), 3.37–3.22 (2 H, m).

Reference Example 13

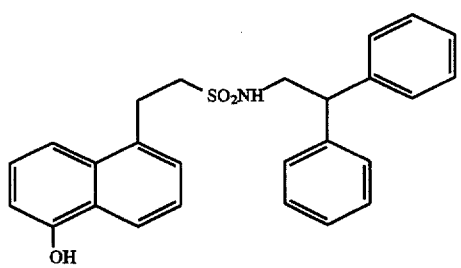

To a solution of the compound prepared in reference example 12 (94.0 g) in methylene chloride (700 ml), boron tribromide (158.6 g) in methylene chloride (300 ml) was added at −30 ° C. The mixture was stirred to warm up to 0 ° C. for 2 hours. The reaction mixture was poured into ice water. The suspension was filtered to collect the white precipitate, which was washed with water, ether, dried over to give the title compound (76.9 g). The combined filtrate was extracted with methylene chloride. The organic layer was washed with water, dried over sodium sulfate and concentrated to give the title compound (9.0 g; total 85.9 g) having following physical data.

TLC: Rf 0.26 (ethyl acetate:hexane=1:2); NMR: δ 8.20 (1 H, d), 7.50–7.10 (14 H, m), 6.87 (1 H, d), 4.05 (1 H, t), 3.59 (2 H, d), 3.50–3.37 (2 H, m), 3.37–3.20 (2 H, m).

Example 5

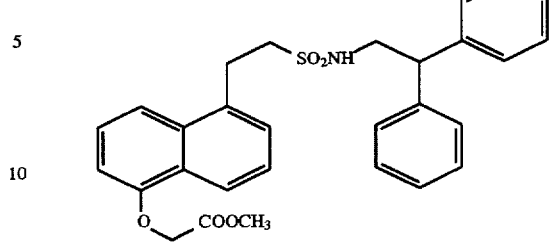

To a solution of the compound prepared in reference example 13 (2.99 g) in DMF (70 ml), sodium bicarbonate (1.10 g) and methyl bromoacetate (1.59 g) was added at room temperature. The mixture was stirred overnight at 100° C. The reaction mixture was filtered to remove the white precipitate and the filtrate was concentrated. The residue was purified by the column chromatography (ethyl acetate:benzene=1:10) to give the title compound (2.33 g) having following physical data.

TLC: Rf 0.23 (ethyl acetate:hexane=1:2); NMR: δ 8.32 (1 H, d), 7.57 (1 H, d), 7.50–7.07 (13 H, m), 6.74 (1 H, d), 4.83 (2 H, s), 4.15–3.93 (2 H, m), 3.82 (3 H, s), 3.61 (2 H, t), 3.53–3.35 (2 H, m), 3.35–3.20 (2 H, m).

Example 6

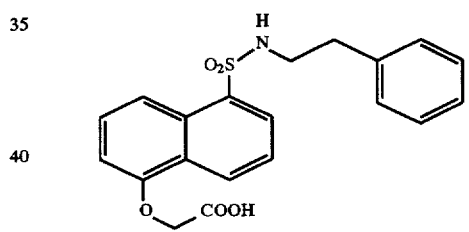

To a solution of the compound prepared in example 4 (0.256 g) in methanol-dimethoxyethane (2 ml–5 ml), 2N aqueous solution of sodium hydroxide (1.5 ml) was added. The mixture was stirred for 3 hours at room temperature. 2N hydrochloric acid was neutralized by adding to the reaction mixture. White precipitate was collected by filtration, and washed with water and ether, and dried over to give the title compound (0.125 mg) having the following physical data. appearance: white powder mp: 174.4–176.2° C.

NMR (CDCl$_3$+CD$_3$OD): δ 8.68(1H, d), 8.23(1H, d), 8.13(1H, d), 7.53(1H, t), 7.50(1H, t), 7.23–7.07(3H, m), 7.00–6.80(3H, m), 4.83(2H, s), 3.13(2H, t), 2.63(2H, t).

Example 6(a)–6(d)

The compounds having the following physical data were obtained by the same procedure as a series of reactions of Reference example 10→Example 4→Example 6.

Example 6(a)

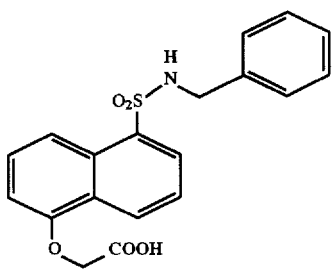

appearance: white powder mp: 200.2°–201.7° C.

NMR (CDCl$_3$+CD$_3$OD): δ 8.67(1 H, d), 8.25(2H, d), 7.54(1H, t), 7.50(1H, t), 7.20–7.00(5H, m), 6.89(1 H, d), 4.83(2H, s), 4.03(2H, s).

Example 6(b)

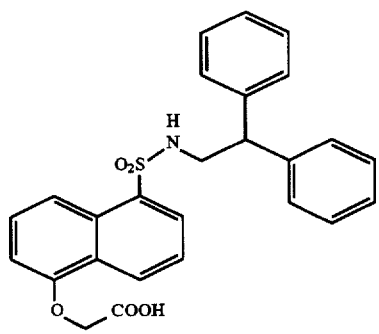

appearance: white powder mp: 198.7–199.0° C.

NMR (CDCl$_3$+CD$_3$OD): δ 8.73(1H, d), 8.28(1H, d), 8.00(1H, d), 7.57(1H, t), 7.42(1H, t), 7.25–7.07(6H, m), 7.00–6.83(5H, m), 4.87(2H, s), 4.00–3.68(1H, m), 3.48(2H, d).

Example 6(c)

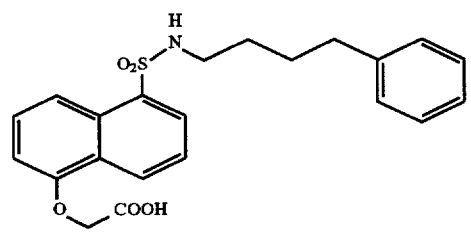

appearance: white powder mp: 162.1°–164.5° C.

NMR (CDCl$_3$+CD$_3$OD): δ 8.67 (1 H, d), 8.23 (2H, d), 7.53 (2H, t), 7.28–7.07 (3H, m), 7.00 (2H, d), 6.88 (1H, d), 4.83 (2H, s), 2.87 (2H, t), 2.43 (2H, t), 1.60–1.27(4H, m).

Example 6(d)

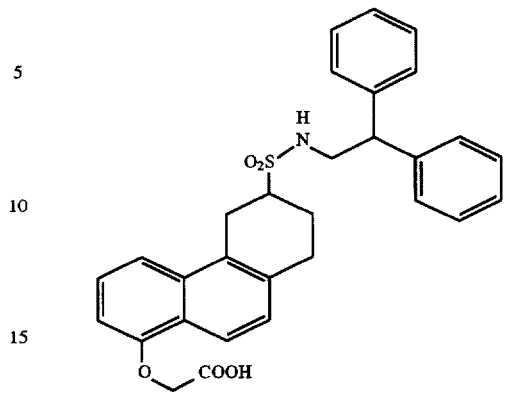

TLC: Rf 0.25 (30% methanol/chloroform) NMR (DMSO-d6): δ 13.02 (1H, brs), 8.00 (1H, d), 7.78–7.18 (13H, m), 6.93 (1H, d), 4.85 (2H, s), 4.22 (1H, t), 4.02–3.80 (1H, m), 3.60–2.80 (7H, m), 2.30–1.80 (2H, m).

Example 6(e)–6(f)

The compounds having the following physical data were obtained by the same procedure as Example 6, using the compound prepared in Example 5, or by the same procedure as the series of reactions of Reference example 11→Reference example 12→Reference example 13→Example 5→Example 6, using a corresponding compound.

Example 6(e)

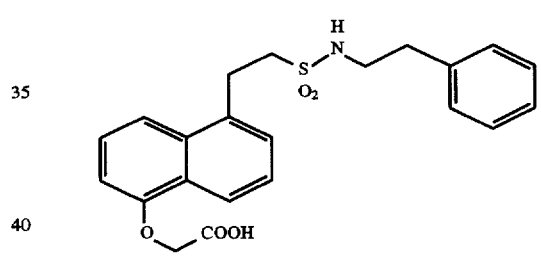

TLC: Rf 0.15 (methanol:methylene chloride=1:5) NMR (CDCl$_3$+CD$_3$OD): δ 8.32 (1 H, d), 7.57 (1 H, d), 7.47–7.10 (8H, m), 6.78 (1H, d), 4.80 (2H, s), 3.53–3.35 (2H, m), 3.35–3.20 (4H, m), 2.78 (2H, t).

Example 6(f)

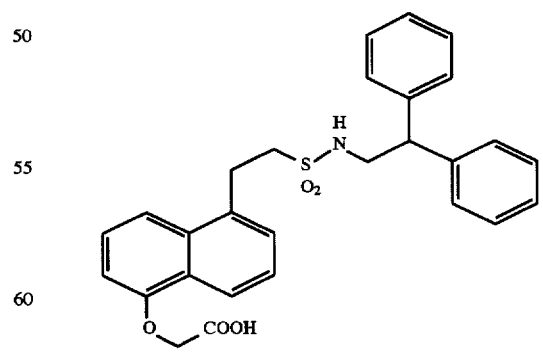

TLC: Rf 0.21 (methanol:methylene chloride=1:5) NMR (DMSO-d6): δ 8.17 (1H, d), 7.57–7.10 (14H, m), 6.91(1H, d), 4.89 (2H, s), 4.18 (1 H, t), 3.67 (2H, m), 3.60–3.00 (4H, m).

Example 7

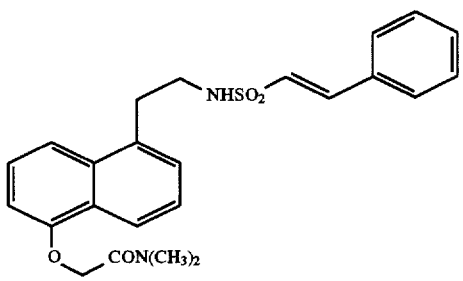

A solution of the compound (0.061 g),-example 2(g), prepared in reference example 1, 2 and example 1 using a corresponding compound in THF (0.5 ml), 50% aqueous solution of dimethylamine (0.1 ml) was added. The mixture was stirred for 4 hours at room temperature. The reaction mixture was diluted with ethyl acetate. The organic layer was washed with 1N aqueous solution of hydrochloric acid and a saturated aqueous solution of sodium chloride, and dried over magnesium sulfate and concentrated. The residue was purified by column chromatography on silica gel (chloroform:methanol=19:1), and crystallized from chloroform-diethyl ether to give the title compound (0.051 g) having the following physical data.

TLC: Rf 0.60 (chloroform:methanol=9:1) NMR: δ 8.24 (1 H, dd), 7.58 (1 H, d), 7.45–7.26 (9H, m), 6.84 (1 H, d), 6.54 (1 H, d), 4.85 (2H, s), 4.47 (1H, t), 3.43 (2H, t), 3.32 (2H, t), 3.13 (3H, s), 3.00 (3H, s).

Example 7(a)–(b)

The compounds having the following physical data were obtained by the same procedure as Example 7.

Example 7 (a)

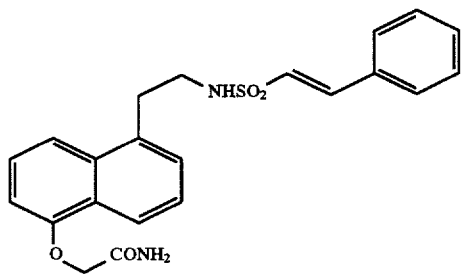

TLC: Rf 0.59 (chloroform:methanol=9:1) NMR: δ 8.14 (1H, dd), 7.66 (1H, d), 7.48–7.32 (9H, m), 6.78 (1H, d), 6.55 (1H, d), 4.63 (2H, s), 3.42–3.30 (4H, m).

Example 7 (b)

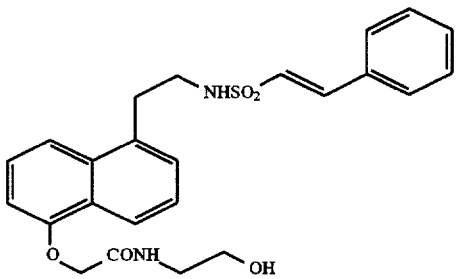

TLC: Rf 0.50 (chloroform:methanol=9:1) NMR (CDCl₃+ CD₃OD): δ 8.16 (1 H, dd), 7.65 (1 H, d), 7.48–7.28 (9H, m), 6.76 (1 H, d), 6.55 (1 H, d), 5.40 (1 H, t), 4.64 (2H, s), 3.73 (2H, t), 3.53 (2H, t), 3.44–3.29 (4H, m).

Example 8

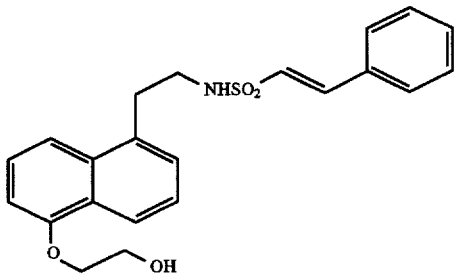

A solution of a compound (0.118 g), example 2(g), prepared in reference example 1, 2 and example 1 using a corresponding compound in methanol-THF (2 ml-1 ml), sodium borohydride (0.057 g) was added. The mixture was stirred for 5 hours at room temperature. The reaction mixture was diluted with ethyl acetate. The organic layer was washed with 1N aqueous solution of hydrochloric acid and a saturated aqueous solution of sodium chloride, and dried over magnesium sulfate and concentrated. The residue was purified by column chromatography on silica gel (hexane:ethyl acetate=2:1) to give the title compound (0.106 g) having the following physical data:

TLC: Rf 0.15 (hexane:ethyl acetate=2:1) NMR (DMSO-d6): δ 8.204 (1H, dd), 7.72–7.57 (4H, m), 7.49–7.34 (6H, m), 7.16 (1H, d), 6.97 (1H, d), 5.01 (1H, t), 4.17 (2H, t), 3.90 (2H, t), 3.38–3.35 (1H, m), 3.28–3.26 (4H, m).

The following species are encompassed by the above examples:

Example 3

5-[(2-phenylvinyl)sulfonylaminomethyl]naphthyloxyacetic acid,

Example 3(a)

5-[(2-phenylvinyl)sulfonylamino]naphthyloxyacetic acid,

Example 3(b)

6-[(2-phenylvinyl)sulfonylamino]naphthyloxyacetic acid,

Example 3(c)

6-[(2-phenylvinyl)sulfonylaminomethyl]naphthyloxyacetic acid,

Example 3(d)
6-[(2,2-diphenylvinyl)sulfonylaminomethyl] naphthyloxyacetic acid,

Example 3(e)
6-[(2,2-diphenylvinyl)sulfonylamino]naphthyloxyacetic acid,

Example 3(f)
5-[(2,2-diphenylvinyl)sulfonylaminomethyl] naphthyloxyacetic acid,

Example 3(g)
5-[2-[(2-phenylvinyl)sulfonylamino]ethyl] naphthyloxyacetic acid,

Example 3(h)
6-[2-[(2-phenylvinyl)sulfonylamino]ethyl] naphthyloxyacetic acid,

Example 3(i)
5-[(2,2-diphenylvinyl)sulfonylamino]naphthyloxyacetic acid,

Example 3(j)
5-[2-[(2,2-diphenylvinyl)sulfonylamino]ethyl] naphthyloxyacetic acid,

Example 3(k)
6-[2-[(2,2-diphenylvinyl)sulfonylamino]ethyl] naphthyloxyacetic acid,

Example 3(l)
6-[(2-phenylvinyl)sulfonylamino]-5,6,7,8-tetrahydronaphthyloxyacetic acid,

Example 3(m)
6-(naphth-2-yl-sulfonylamino)-5,6,7,8-tetrahydronaphthyloxyacetic acid,

Example 3(n)
6-[(2,2-diphenylvinyl)sulfonylamino]-5,6,7,8-tetrahydronaphthyloxyacetic acid,

Example 3(o)
5-[(2-phenylvinyl)sulfonylamino]-5,6,7,8-tetrahydronaphthyloxyacetic acid,

Example 3(p)
5-[(2,2-diphenylvinyl)sulfonylamino]-5,6,7,8-tetrahydronaphthyloxyacetic acid,

Example 3(q)
5-(naphth-2-yl-sulfonylamino)-5,6,7,8-tetrahydronaphthyloxyacetic acid,

Example 3(r)
6-[(2-phenylvinyl)sulfonylaminomethyl]-5,6,7,8-tetrahydronaphthyloxy acetic acid,

Example 3(s)
5-[2-[(2-phenylvinyl)sulfonylamino]ethyl]-5,6,7,8-tetrahydronaphthyloxyacetic acid,

Example 3(t)
5-[3-[(2-phenylvinyl)sulfonylamino]propyl] naphthyloxyacetic acid,

Example 3(u)
5-[3o[(2,2-diphenylvinyl)sulfonylamino]propyl] naphthyloxyacetic acid,

Example 3(v)
5-[(2-phenylethyl)sulfonylamino]naphthyloxyacetic acid,

Example 3(w)
5-[2-[(2-phenylethyl)sulfonylamino]ethyl] naphthyloxyacetic acid,

Example 3(x)
5-(pentylsulfonylamino)naphthyloxyacetic acid,

Example 3(y)
6-[(2-phenylvinyl)sulfonylaminomethyl]naphth-3-yloxyacetic acid,

Example 3(z)
5-[2-[(2-phenylethyl)sulfonylamino]ethyl]-7,8-dihydronaphthyloxy acetic acid,

Example 3(aa)
5-[2-[(2-phenylvinyl)sulfonylamino]ethyl]-7,8-dihydronaphthyloxyacetic acid,

Example 3(bb)
6-[(2-phenylvinyl)sulfonylaminomethyl]-5,6,7,8-dihydronaphth-3-yl-oxyacetic acid,

Example 3(cc)
5-[2-[(2,2-diphenylethyl)sulfonylamino]ethyl] naphthyloxyacetic acid,

Example 3(dd)
5-[2-[(2-phenylvinyl)sulfonyl-N-ethylamino]ethyl] naphthyloxyacetic acid,

Example 3(ee)
5-[2-[(2-phenylvinyl)sulfonyl-N-carboxymethylamino] ethyl]naphthyloxyacetic acid,

Example 3(gg)
5-[2-[[2-(4-methoxyphenyl)-2-phenylethyl]sulfonylamino] ethyl]naphthyloxyacetic acid,

Example 3(hh)
5-[2-[(2-phenylpropyl)sulfonylamino]ethyl] naphthyloxyacetic acid,

Example 3(ii)
5-[2-[(2-cyclohexyl-2-phenylethyl)sulfonylamino]ethyl] naphthyl oxyacetic acid,

Example 3(jj)
5-[2-[[2-(4-methoxyphenyl)vinyl]sulfonylamino]ethyl] naphthyloxyacetic acid,

Example 3(kk)

5-[2-[[2-(4-chlorophenyl)-2-phenylvinyl]sulfonylamino]ethyl]naphthyl oxyacetic acid,

Example 3(ll)

5-[2-[[2-(4-chlorophenyl)vinyl]sulfonylamino]ethyl]naphthyloxyacetic acid,

Example 7

5-[2-[(2-phenylvinyl)sulfonylamino]ethyl]-1-N,N-dimethylaminocarbonyl methyloxynaphthalene,

Example 7(a)

5-[2-[(2-phenylvinyl)sulfonylamino]ethyl]naphthyloxyacetamide,

Example 7(b)

5-[2-[(2-phenylvinyl)sulfonylamino]ethyl]-1-(2-hydroxyethyl)amino carbonylmethyloxynaphthalene,

Example 8

5-[2-[(2-phenylvinyl)sulfonylamino]ethyl]-1-(2-hydroxyethyl)oxynaphthalene,

Example 3(ff)

6-[(2-phenylvinyl)sulfonylamino]-5,6,7,8-tetrahydrophenanthrene-1-yl-oxyacetic acid,

Example 6

5-[N-(2-phenylethyl)sulfamoyl]naphthyloxyacetic acid,

Example 6(a)

5-(N-phenylmethylsulfamoyl)naphthyloxyacetic acid,

Example 6(b)

5-[N-(2,2-diphenylethyl)sulfamoyl]naphthyloxyacetic acid,

Example 6(c)

5-[N-(4-phenylbutyl)sulfamoyl]naphthyloxyacetic acid,

Example 6(f)

5-[2-[N-(2,2-diphenylethyl)sulfamoyl]ethyl]naphthyloxyacetic acid,

Example 6(e)

5-[2-[N-(2-phenylethyl)sulfamoyl]ethyl]naphthyloxyacetic acid, and

Example 6(d)

6-[(2,2-diphenylethyl)sulfamoyl]-5,6,7,8-tetrahydrophenanthren-1-yl-oxyacetic acid.

Formulation Example 1

The following compounds were admixed in conventional method and punched out to obtain 100 tablets each containing 5 mg of active ingredient.

5-[(2-phenylvinyl)sulfonylamino methyl]naphthyloxy acetic acid ... 500 mg

Carboxymethylcellulose calcium ... 200 mg

Magnesium stearate ... 100 mg

Micro crystalline cellulose ... 9.2 g

What is claimed:

1. A compound of the formula (I):

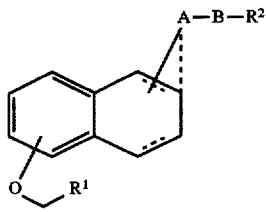

wherein

R$^1$ is (i) —COOR$^4$ in which R$^4$ is hydrogen or C1–4 alkyl, (ii) —CONR$^5$R$^6$ in which R$^5$ and R$^6$ each, independently, is hydrogen, C1–4 alkyl or C1–4 alkyl substituted by 1 of hydroxy, or (iii) —CH$_2$OH,

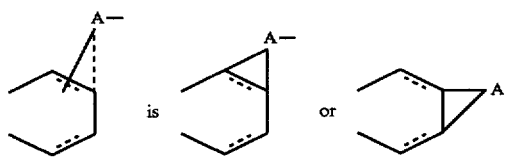

in which A is

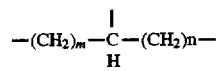

in which m is 0, 1, 2, 3, 4, n is 0, 1, 2, 3, 4, and m+n is 2, 3, 4;

B is —NR$^3$SO$_2$— or —SO$_2$NR$^3$— in which R$^3$ is hydrogen, C1–4 alkyl or —CH$_2$COOR$^7$ in which R$^7$ is hydrogen or R$^{4a}$, in which R$^{4a}$ is C1–4 alkyl;

R$^2$ is (i) C1–6 alkyl, C2–6 alkenyl or C2–6 alkynyl, (ii) C1–6 alkyl, C2–6 alkenyl or C2–6 alkynyl substituted by 1, 2, 3 of phenyl, C4–7 cycloalkyl or phenyl substituted by 1, 2, 3 of C1–4 alkyl, C1–4 alkoxy or halogen or (iii) naphthyl; and in the formula

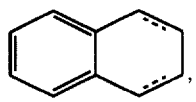

- - - - - - is a bond or a double bond;

or a pharmaceutically acceptable salt thereof.

2. A compound according to claim 1, wherein B is —NR$^3$SO$_2$, in which R$^3$ has the same meaning as defined in claim 1.

3. A compound according to claim 1, wherein B is —SO$_2$NR$^3$, in which R$^3$ has the same meaning as defined in claim 1.

4. A compound according to claim 1, which is 6-[(2-phenylvinyl)sulfonylamino]-5,6,7,8-tetrahydrophenanthrene-1-yl-oxyacetic acid.

5. A compound according to claim 1, which is 6-[(2,2-diphenylethyl)sulfamoyl]-5,6,7,8-tetrahydrophenanthren-1-yl-oxyacetic acid.

6. A pharmaceutical composition for the prevention and/ or treatment of abortion, pain, diarrhea, insomnia, constipation, ulcer, gastritis or hypertension, or for inducing labor in pregnant female mammals, which comprises, as the active ingredient, an effective amount of a naphthyloxyacetic acid of the formula (I) depicted in claim 1 or non-toxic salts thereof, with a pharmaceutical carrier or coating.

* * * * *